United States Patent [19]
Hansen et al.

[11] Patent Number: 5,571,618
[45] Date of Patent: * Nov. 5, 1996

[54] REACTIVATABLE BINDERS FOR BINDING PARTICLES TO FIBERS

[75] Inventors: Michael R. Hansen, Seattle; Richard H. Young, Sr., Renton, both of Wash.

[73] Assignee: Weyerhaeuser Company, Federal Way, Wash.

[*] Notice: The term of this patent shall not extend beyond the expiration date of Pat. No. 5,352,480.

[21] Appl. No.: 261,811

[22] Filed: Jun. 17, 1994

Related U.S. Application Data

[63] Continuation of Ser. No. 931,278, Aug. 17, 1992, Pat. No. 5,352,480.

[51] Int. Cl.$^6$ .................................................. D02G 3/00
[52] U.S. Cl. .................... 428/359; 428/357; 428/364; 428/372; 428/375; 428/393
[58] Field of Search .................................... 428/375, 378, 428/393, 372, 359, 357, 364

[56] References Cited

U.S. PATENT DOCUMENTS

| | | | |
|---|---|---|---|
| 2,601,597 | 6/1952 | Daniel, Jr. et al. | 92/21 |
| 2,953,187 | 9/1960 | Francis, Jr. | 154/29 |
| 3,010,161 | 11/1961 | Duvall | 19/156 |
| 3,021,242 | 12/1962 | Touey | 156/180 |
| 3,059,313 | 10/1962 | Harmon | 28/80 |

(List continued on next page.)

FOREIGN PATENT DOCUMENTS

| | | |
|---|---|---|
| 729513 | 6/1962 | Canada. |
| 806352 | 4/1964 | Canada. |
| 841940 | 12/1965 | Canada. |
| 813616 | 12/1965 | Canada. |
| 953 890 | 9/1974 | Canada. |
| 1052156 | 12/1976 | Canada. |

(List continued on next page.)

OTHER PUBLICATIONS

Amosov et al., "Aluminum hydroxy compounds–binders for dry–process paper," *Izv. VUZ, Lesnoi Zh.*, 6:72–76 (1986).
Blanchard and Reinhart, "Dyeing of Crosslinked Cotton Containing Glycol Additives," *U.S. Dept. of Agriculture*, New Orleans, 24:13–17 (Jan. 1992).
Burkholder, "Absorbent Polymers–A New Concept in Fluid Absorption," *The Dow Chemical Company Designed Products Laboratory*, Midland, Michigan, pp. 73–79 (1973).

(List continued on next page.)

*Primary Examiner*—Patrick J. Ryan
*Assistant Examiner*—J. M. Gray
*Attorney, Agent, or Firm*—Christensen O'Connor Johnson & Kindness PLLC

[57] ABSTRACT

Particles, such as superabsorbent particles, are bound to fibers, such as cellulosic fibers, by a binder that has a volatility less than water. The binder has a functional group capable of forming a hydrogen bond with the fibers, and a functional group that is capable of forming a hydrogen bond or a coordinate covalent bond with the particles. The binder is activated or reactivated by addition of heat, liquid, or mechanical energy. Therefore, fibers treated with binder may be shipped to a distribution point before particles are bound to the fibers. The binder may be a polymeric binder selected from the group consisting of polyethylene glycol, polypropylene glycol, poly (caprolactone) diol, polyacrylic acid, polyamides and polyamines. The polymeric binder has a hydrogen bonding functionality or coordinate covalent bond forming functionality on each repeating unit of the polymeric binder. Alternatively, the binder may be a nonpolymeric organic binder that includes a functionality such as a carboxylic acid, an aldehyde, an alcohol, an amino acid, an amide, and an amine, wherein there are at least two such functionalities on the molecule. Particles attached to the fibers in this manner are firmly adhered and are not easily dislodged. Fibrous products produced by this method include fibers to which particles are bound, and fibers which have been treated with the binder but to which particles are not bound.

34 Claims, 8 Drawing Sheets

U.S. PATENT DOCUMENTS

| | | | |
|---|---|---|---|
| 3,070,095 | 12/1962 | Torr | 128/284 |
| 3,087,833 | 4/1963 | Drelich | 117/38 |
| 3,327,708 | 6/1967 | Sokolowski | 128/156 |
| 3,344,789 | 10/1967 | Arnold et al. | 128/287 |
| 3,377,302 | 4/1968 | Gugliemelli et al. | 260/17.4 |
| 3,395,201 | 7/1968 | Kalwaites | 264/45 |
| 3,425,971 | 2/1969 | Gugliemelli et al. | 260/17.4 |
| 3,494,992 | 2/1970 | Wiegand | 264/121 |
| 3,521,638 | 7/1970 | Parrish | 128/284 |
| 3,554,788 | 1/1971 | Fechillas | 117/140 |
| 3,661,154 | 5/1972 | Torr | 128/284 |
| 3,661,632 | 5/1972 | Gagliardi et al. | 117/143 A |
| 3,669,103 | 6/1972 | Harper et al. | 128/156 |
| 3,670,731 | 6/1972 | Harmon | 128/284 |
| 3,672,945 | 6/1972 | Taylor | 117/100 B |
| 3,692,622 | 9/1972 | Dunning | 161/124 |
| 3,745,060 | 7/1973 | Jumentier et al. | 161/170 |
| 3,766,922 | 10/1973 | Krusko | 128/284 |
| 3,777,758 | 12/1973 | Mesek et al. | 128/284 |
| 3,788,936 | 1/1974 | Brock et al. | 161/148 |
| 3,804,092 | 4/1974 | Tunc | 128/284 |
| 3,808,088 | 4/1974 | Knechtges et al. | 161/148 |
| 3,886,941 | 6/1975 | Duane et al. | 128/287 |
| 3,888,256 | 6/1975 | Studinger | 128/296 |
| 3,888,257 | 6/1975 | Cook et al. | 128/296 |
| 3,901,236 | 9/1975 | Assarsson et al. | 128/284 |
| 3,903,889 | 9/1975 | Torr | 128/287 |
| 3,908,659 | 9/1975 | Wehrmeyer et al. | 128/287 |
| 3,923,592 | 12/1975 | George et al. | 162/168 |
| 3,949,035 | 4/1976 | Dunning et al. | 264/90 |
| 3,978,257 | 8/1976 | Ring | 428/137 |
| 3,991,237 | 11/1976 | Topfl et al. | 427/386 |
| 4,007,083 | 2/1977 | Ring et al. | 162/101 |
| 4,009,313 | 2/1977 | Crawford et al. | 428/290 |
| 4,035,217 | 7/1977 | Kennette et al. | 156/279 |
| 4,055,180 | 10/1977 | Karami | 128/287 |
| 4,061,268 | 12/1977 | DeMaster | 238/14 |
| 4,062,451 | 12/1977 | Gander | 206/524.2 |
| 4,071,636 | 1/1978 | Nishino et al. | 427/2 |
| 4,102,340 | 7/1978 | Mesek et al. | 128/287 |
| 4,103,062 | 7/1978 | Aberson et al. | 428/283 |
| 4,160,059 | 7/1983 | Samejima | 428/288 |
| 4,232,674 | 11/1979 | Melican | 128/287 |
| 4,250,660 | 2/1981 | Kitamura et al. | 47/57.6 |
| 4,282,121 | 8/1981 | Goodrich | 260/17.4 GC |
| 4,289,513 | 9/1981 | Brownhill et al. | 55/387 |
| 4,289,536 | 9/1981 | Dereser | 106/99 |
| 4,324,706 | 4/1982 | Tabe et al. | 523/149 |
| 4,364,992 | 12/1982 | Ito et al. | 428/283 |
| 4,379,194 | 4/1983 | Clarke et al. | 428/203 |
| 4,394,172 | 7/1983 | Scheuble et al. | 106/38.5 D |
| 4,404,250 | 9/1983 | Clarke | 428/220 |
| 4,410,571 | 10/1983 | Korpman | 427/385.5 |
| 4,412,036 | 10/1983 | Pederson et al. | 525/54.26 |
| 4,424,247 | 1/1984 | Erickson | 428/138 |
| 4,457,978 | 7/1984 | Wawzonek | 524/14 |
| 4,467,012 | 8/1984 | Pederson et al. | 428/248 |
| 4,486,501 | 12/1984 | Holbek | 428/375 |
| 4,492,729 | 1/1985 | Bannerman et al. | 428/283 |
| 4,532,176 | 7/1985 | Briggs et al. | 428/288 |
| 4,537,767 | 8/1985 | Rothman et al. | 424/78 |
| 4,558,091 | 12/1985 | Hubbard | 524/734 |
| 4,597,930 | 7/1986 | Szal | 264/115 |
| 4,673,402 | 6/1987 | Weisman et al. | 604/368 |
| 4,676,784 | 6/1987 | Erdman et al. | 604/368 |
| 4,758,466 | 7/1988 | Dabi et al. | 428/283 |
| 4,772,492 | 9/1988 | Bouchette | 427/342 |
| 4,788,080 | 11/1988 | Hojo et al. | 427/204 |
| 4,818,599 | 4/1989 | Marcus | 428/288 |
| 4,826,880 | 5/1989 | Lesniak et al. | 521/53 |
| 4,833,011 | 5/1989 | Horimoto | 428/288 |
| 4,842,593 | 7/1989 | Jordan et al. | 604/360 |
| 4,874,811 | 10/1989 | Borchers et al. | 524/516 |
| 4,886,697 | 12/1989 | Perdelwitz, Jr. et al. | 428/192 |
| 4,892,769 | 1/1990 | Perdelwitz, Jr. et al. | 428/68 |
| 4,902,565 | 2/1990 | Brook | 428/315.5 |
| 5,002,814 | 3/1991 | Knack et al. | 428/85 |
| 5,057,166 | 10/1991 | Young, Sr. et al. | 156/62.2 |
| 5,064,689 | 11/1991 | Young, Sr. et al. | 427/202 |
| 5,128,082 | 7/1992 | Makoui | 264/112 |
| 5,161,686 | 11/1992 | Weber et al. | 206/440 |
| 5,217,445 | 6/1993 | Young et al. | 604/381 |
| 5,225,047 | 7/1993 | Graef et al. | 162/9 |
| 5,230,959 | 7/1993 | Young, Sr. et al. | 428/372 |
| 5,252,275 | 10/1993 | Sultze et al. | 264/119 |
| 5,252,340 | 10/1993 | Honeycutt | 424/489 |
| 5,278,222 | 1/1994 | Stack | 524/502 |
| 5,283,123 | 2/1994 | Carter et al. | 428/403 |
| 5,300,054 | 4/1994 | Feist et al. | 604/378 |
| 5,300,192 | 4/1994 | Hansen et al. | 162/184 |
| 5,312,522 | 5/1994 | Van Phan et al. | 162/111 |

FOREIGN PATENT DOCUMENTS

| | | |
|---|---|---|
| 122042 | 10/1984 | European Pat. Off. . |
| 0 427 316 A2 | 7/1989 | European Pat. Off. . |
| 0 429 112 A2 | 7/1989 | European Pat. Off. . |
| 0 427 317 A2 | 7/1989 | European Pat. Off. . |
| 0 440 472 A1 | 1/1990 | European Pat. Off. . |
| 0 442 185 A1 | 8/1991 | European Pat. Off. . |
| 1 382 716 | 2/1964 | France . |
| 489 308 | 1/1930 | Germany . |
| 1 079 796 | 6/1962 | Germany . |
| 2 048 721 | 6/1971 | Germany . |
| 61-28422 | 2/1986 | Japan . |
| 1 217 452 | 12/1969 | United Kingdom . |
| 2189127 | 10/1987 | United Kingdom . |
| WO88/01316 | 2/1988 | WIPO . |
| WO90/09236 | 8/1990 | WIPO . |
| WO90/11181 | 10/1990 | WIPO . |

OTHER PUBLICATIONS

Byrd, "How bonds develop during web consolidation," *PTI*, pp. 240–243 (Oct. 1986).

Gorbushin et al., "Investigation of the effect of the nature and concentration of binders on the properties of dry–process paper," *Sb. Tr. Tsentr. Nauch.–Issled. Inst. Bumagi*, 9:117–123 (1974).

Gugliemelli et al., "Base–Hydrolyzed Starch–Polyacrylonitrile (S–PAN) Graft Copolymer. S–PAN–1:1, PAN M. W. 794,000*", *J. of Applied Copolymer Science*, 13:2007–2017 (1969).

Hoque et al., "Granulation and Tabletting of Iron Oxide–Chromic Oxide Catalyst Mass with the Aid of Binding Ingredients Part II–Cellulosic Derivatives and Polyethylene Glycol as Binding Ingredients," *Fertilizer Technology*, 20:30–35 (1983).

Lindsay, "Absorbent Starch Based Co–polymers–Their Characteristics and Applications," *Formed Fabrics Industry*, pp. 20, 24 and 26 (May 1977).

Lysogorskaya et al., "Effect of Moisture Content on the Development of Interfiber Bonds in Air–Laid Paper," *Leningrad Technological Institute of the Pulp and Paper Industry*, Zh. Prikl, Khim., 63:(8) 1869–1872 (1990).

Lysogorskaya et al., "Effect of Moisture Content on Development of Interfiber Bonding in the Structure of Air–Dried Paper," *Plenum Publ. Corp.*, pp. 1730–1733 (1991).

Ogurtsov et al., "Effect of the modulus of elasticity of the binder on the properties of dry–process paper," *Sb. Tr. Tsentr. Nauch.–Issled. Inst. Bumagi*, 9:123–127 (1974).

S. Lammie, "Use of Glycerine as a Softener for Paper Products," *The World's Paper Trade Review*, p. 2050, Dec. 13, 1962.

Sliwiok and Kowalska, "Investigation of Self–Association of the Selected Glycols and Cellulose Sorbents," *Microchemical Journal*, 26:68–74 (Jan. 1992).

"Super slurpers: Time for change?," *Chemical Week*, pp. 21–22 Jul. 24, 1974.

Weaver et al., "Hydrolyzed Starch–Polyacrylonitrile Graft Copolymers: Effect of Structure on Properties*", *J. of Applied Polymer Science*, 15:3015–3024 (1971).

Weaver et al., "Highly Absorbent Starch–Based Polymer," *Northern Regional Research Laboratory, Agricultural Research Service*, U.S. Dept. of Agriculture, Peoria, Illinois, pp. 169–177.

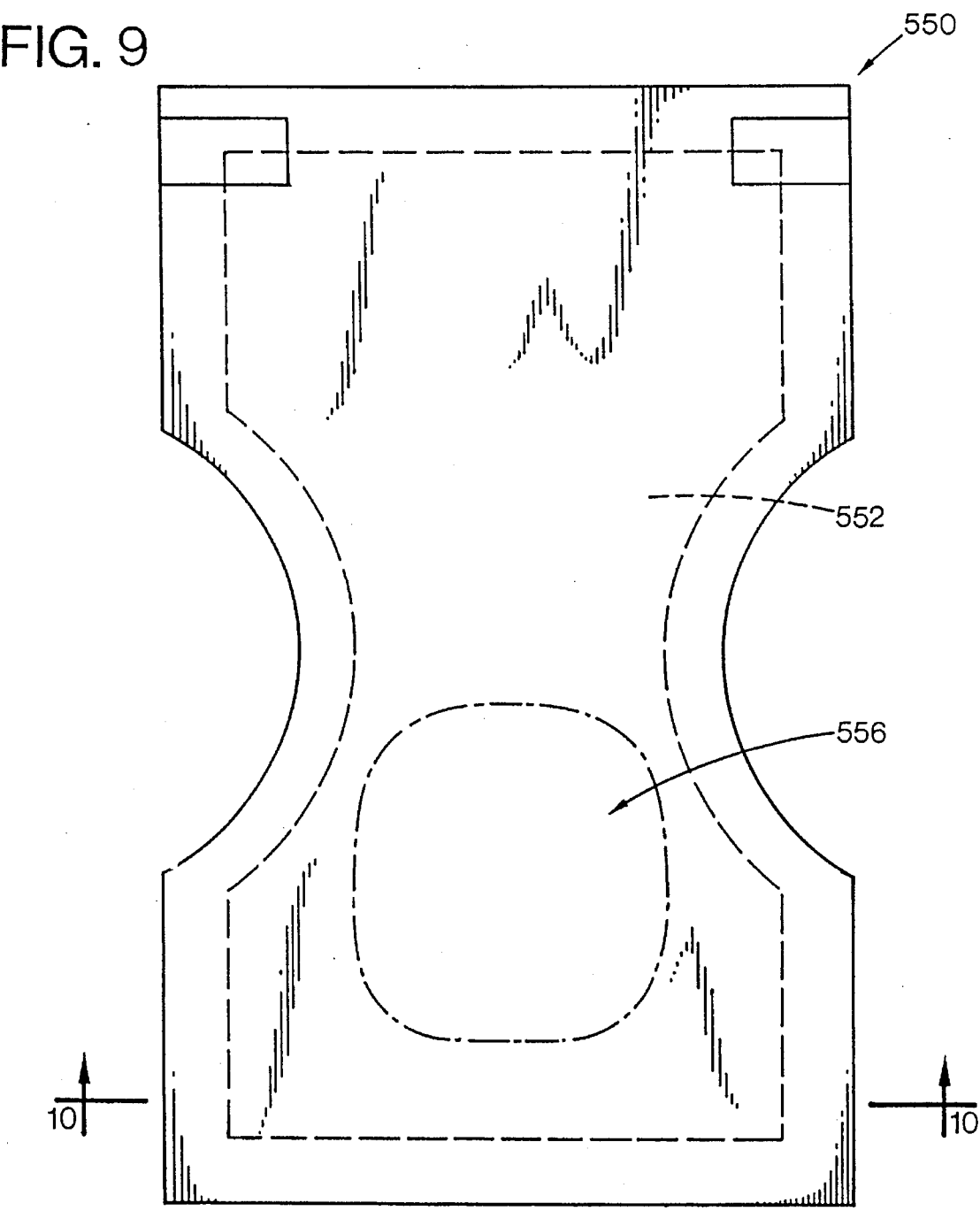

REACTIVATABLE BINDERS FOR BINDING PARTICLES TO FIBERS

This is a continuation of the prior application Ser. No. 07/931,278, filed Aug. 17, 1992, now U.S. Pat. No. 5,352, 480, the benefit of the filing date of which is hereby claimed under 35 U.S.C. § 120.

BACKGROUND OF THE INVENTION

1. Field of the Invention

This invention concerns reactivatable polymeric and non-polymeric binders for fibers and the use of such binders in binding particles to fibers. In particular embodiments, it concerns binding superabsorbent particles to cellulosic fibers which may then be used, for example, to make absorbent fibers that are incorporated into cellulosic products.

2. General Discussion of the Background

Superabsorbent polymers have been developed in recent years that are capable of absorbing many times their own weight of liquid. These polymers, which are also known as water insoluble hydrogels, have been used to increase the absorbency of sanitary products such as diapers and sanitary napkins. Superabsorbent polymers are often provided in the form of particulate powders, granules, or fibers that are distributed throughout absorbent cellulosic products to increase the absorbency of the product. Superabsorbent particles are described, for example, in U.S. Pat. No. 4,160, 059; U.S. Pat. No. 4,676,784; U.S. Pat. No. 4,673,402; U.S. Pat. No. 5,002,814; and U.S. Pat. No. 5,057,166. Products such as diapers that incorporate absorbent hydrogels are shown in U.S. Pat. No. 3,669,103 and U.S. Pat. No. 3,670, 731.

One problem with the use of superabsorbents is that the superabsorbent material can be physically dislodged from the cellulosic fibers of an absorbent product. Separation of the superabsorbent from its substrate reduces the absorbency of the product and diminishes the effectiveness of the superabsorbent material. This problem was addressed in European Patent Application 442 185 A1, which discloses use of a polyaluminum chloride binder to bind an absorbent polymer to a fibrous substrate. The polyaluminum binder, however, suffers from the drawback of being an inorganic product that is not readily biodegradable. Moreover, that European patent does not offer any guidance for selecting binders other than polyaluminum chloride that would be useful in binding absorbent particles.

A method of immobilizing superabsorbents is disclosed in U.S. Pat. No. 4,410,571 in which a water swellable absorbent polymer is converted to a non-particulate immobilized confluent layer. Polymer particles are converted to a coated film by plasticizing them in a polyhydroxy organic compound such as glycerol, ethylene glycol, or propylene glycol. The superabsorbent assumes a non-particulate immobilized form that can be foamed onto a substrate. The individual particulate identity of the superabsorbent polymer is lost in this process. The confluent nature of the superabsorbent material can also result in gel blocking, in which absorption is diminished as the water swollen polymers block liquid passage through the film layer.

U.S. Pat. No. 4,412,036 and U.S. Pat. No. 4,467,012 disclose absorbent laminates in which a hydrolyzed starch polyacrylonitrile graft copolymer and glycerol mixture is laminated between two tissue layers. The tissue layers are laminated to each other by applying external heat and pressure. The reaction conditions form covalent bonds between the tissue layers that firmly adhere the tissue layers to one another.

Numerous other patents have described methods of applying binders to fibrous webs. Examples include U.S. Pat. No. 2,757,150; U.S. Pat. No. 4,584,357; and U.S. Pat. No. 4,600,462. Such binders are not described as being useful in binding particulates, such as superabsorbent particles, to fibers. Yet other patents disclose crosslinking agents such as polycarboxylic acids that form covalent intrafiber bonds with individualized cellulose fibers, as in European Patent Application 440472 A1; European Patent Application 427 317 A2; European Application 427 316 A2; and European Patent Application 429 112 A2. The covalent intrafiber bonds are formed at elevated temperatures and increase the bulk of cellulose fibers treated with the crosslinker. The covalent bonds between the fibers produce a pulp sheet that is more difficult to compress to conventional pulp sheet densities than in an untreated sheet. Any covalent crosslink bonds that form between the fibers and particles occupy functional groups that would otherwise be available for absorption, hence absorption efficiency is decreased.

Many different types of particles other than superabsorbents may be added to fibers for different end uses. Antimicrobials, zeolites and fire retardants are but a few examples of particles that are added to fibers. It would be advantageous to provide a method of attaching particles that could be accommodated to the many different particle needs of end users. Moreover, it would be advantageous to reduce particulate waste in the attachment process, and simplify shipment of fiber products that require particulate addition.

Accordingly, it is an object of this invention to provide an improved method of binding particulates to fibers which can be customized to easily allow different end users of the products to bind different kinds of particles to the fibers.

It is also an object of this invention to provide an improved method of binding particulates, such as superabsorbent particles, to fibers.

It is another object to provide an improved method of binding particulates such that they can be distributed throughout a fibrous product in a desired distribution and without necessarily being confined to the surface of a product.

Another object of the invention is to provide improved fiber and absorbent products in which particulates are firmly bound to cellulose fibers such that the particles are less likely dislodged by mechanical forces.

Yet another object of the invention is to provide an improved particle binder that is environmentally compatible and more easily biodegradable.

Even yet another object is to provide such a product that has improved processing characteristics, such as ease of densification.

Finally, it is an object of the invention to bind a broad variety of particles to many different kinds of fibers using an improved, simple and versatile binding process that limits particle waste.

SUMMARY OF THE INVENTION

The foregoing and other objects are achieved by providing fibers with hydrogen bonding functional sites, and applying to the fibers a binder that has a volatility less than water. The binder has a functional group that forms a hydrogen bond with the fibers, and a functional group that is also capable of forming a hydrogen bond or a coordinate covalent bond with particles that have a hydrogen bonding or coordinate covalent bonding functionality. The binder attaches the particles to the fibers, and forms a bond that has been found to be resistant to mechanical disruption. A significant advantage of these binders is that the binders can be present on fibers in an inactive state, then later activated or reactivated to bind particles to the fibers.

Liquid binders (which includes aqueous solutions of solid binders or neat liquids) can be placed on the fibers, air dried, and later reactivated by moistening the fibers. Alternatively, a dry solid binder may be added to the fibers and later activated by addition of a liquid. An inactive binder can also be activated by applying kinetic energy to the fibers after the binder and fibers reach an equilibrium moisture content with the atmosphere (hereinafter referred to as "air drying"). Kinetic energy can be applied to the fibers, for example, by mechanically agitating the binder and fibers. In yet other embodiments, the binder may be activated or reactivated by the fibers after applying the binder to the fibers.

The capacity for activation or reactivation allows the binder be applied to the fibers, which are then shipped to distribution points with the binder in an inactive form. The binder is then activated at the distribution point where particles are added to the fibers and bound thereto. As used herein, binder "activation" includes both activation of previously inactive binders (such as solid binders in the absence of liquid) or reactivation of previously active binders such as a liquid binder that has been air dried).

Another advantage of the present Invention is that the binder can be activated or reactivated in a pattern that corresponds to a desired distribution of particles in fibrous material. A reactivation liquid, for example, can be applied to the areas of a diaper that will be initially moistened by urine during use. Superabsorbent particles can be added to activated area of the diaper and adhered almost exclusively in those areas where initial urine absorption is required. Targeted activation of binder allows particles to be efficiently and economically attached to the fibers, with reduced particle wastage. Moreover, targeted binder activation and particle adherence increases the absorptive efficiency of the product by diminishing excessive wicking of liquid within the plane of an absorptive product.

The fibers of the present invention may have particles bound to the fibers with a polymeric or non-polymeric binder. The polymeric binder may be polypropylene glycol (PPG), polyethylene glycol (PEG), polyacrylic acid (PAA), a poly(caprolactone) diol, polyamide, a polyamine, and copolymers thereof (for example a polypropylene glycol/polyethylene glycol copolymer), wherein the polymeric binder has a hydrogen bonding functionality or coordinate covalent bond forming functionality on each repeating unit of the polymeric binder. In the present invention, the non-polymeric has a volatility less than water, a functional group that forms hydrogen bonds or coordinate covalent bonds with the particles, and a functional group that forms hydrogen bonds with the cellulose fibers. The non-polymeric binder is an organic binder, and preferably includes a functionality selected from the group consisting of a carboxylic acid, an aldehyde, an alcohol, an amino acid, an amide, and an amine, wherein there are at least two functionalities on the molecule selected from this group, and the two functionalities are the same or different. Examples of such binders include polyols, polyamines (a non-polymeric organic binder with more than one amine group), polyamides (a non-polymeric organic binder with more than one amide group), polycarboxylic acids (a non-polymeric organic binder with more than one carboxylic acid functionality), a polyaldehyde (a non-polymeric organic binder with more than one aldehyde), amino alcohols, hydroxy acids and other binders. These binders have functional groups that are capable of forming the specified bonds with the particles and fibers.

More preferably, the organic non-polymeric binder is selected from the group consisting of glycerin, glyoxal, ascorbic acid, urea, glycine, pentaerythritol, a monosaccharide or a disaccharide, citric acid, tartaric acid, dipropylene glycol, and urea derivatives such as DMDHEU. Suitable saccharides include glucose, sucrose, lactose, ribose, fructose, mannose, arabinose, and erythrose. Each of these preferred binders is a non-polymeric molecule that has a plurality of hydrogen bonding functionalities that permit the binder to form hydrogen bonds to both the fibers and particles. Particularly preferred binders include those that can form five or six membered rings, most preferably six membered rings, with a functional group on the surface of the particle.

The fibrous material may be cellulosic or synthetic fibers that are capable of forming hydrogen bonds with the binder, while the particles form hydrogen or coordinate covalent bonds with the binder. This binder system secures particles to fibers unexpectedly well. A superior fibrous product is therefore produced that has improved absorbent properties as compared to unbound or covalently bound particles. Formation of the noncovalent bond allows production of a fiber product that is easily manufactured and a web that is easily densified, and that is readily biodegradable and disposable.

In one preferred embodiment, an absorbent product comprises a fibrous cellulosic mat that contains superabsorbent hydrogel particles in particulate form. The superabsorbent particles form hydrogen bonds or coordinate covalent bonds with the binder, depending upon the binder, while the binder in turn forms hydrogen bonds with the hydroxyl groups of the cellulose fibers. These noncovalent, relatively flexible bonds between the binder and particles maintain the particles in contact with the fibers, and resist dislodgement of the particles by mechanical forces applied to the mat during manufacture, storage or use. The binder may suitably be present in an amount of from about 3 to 80 percent of the total weight of the product, while the particles bound to the binder of the present invention (via hydrogen/coordinate covalent bonds) may suitably be present in an amount of 0.05 to 80 percent, preferably 1 to 80 percent or 5 to 80 percent by weight. An especially suitable range of binder is 3 to 40 percent by weight, or 3 to 25 percent by weight, while a particularly suitable range of such particles is 5 to 40 percent by weight. A preferred weight ratio of particle to binder is 2:1 to 4:1. An example of a suitable particle is a superabsorbent polymer such as a starch graft polyacrylate hydrogel fine or larger size particle such as a granule, which forms hydrogen bonds with the binder. The binder also forms hydrogen bonds with the hydroxyl groups of the cellulose, thereby securely attaching the superabsorbent particles to the fibers.

The present invention also includes a method of binding particles to fibers wherein the particles are insoluble in the binder and therefore retain their solid particulate form following binding. The particles have functional groups that can form hydrogen bonds or coordinate covalent bonds with the binder, and the binder in turn is capable of forming hydrogen bonds to the fibers.

In especially preferred embodiments, the fibers are cellulosic and the particles are superabsorbent particles that are bound to the binder by hydrogen bonds. The fibers may also be continuous or discontinuous synthetic or natural fibers having a hydrogen bonding functional group that hydrogen bonds with the binder. The binder is suitably applied to the fibers in an amount of at least 3 percent, and preferably no more than 80 percent, by total weight of the particle, fiber and binder. The particles may be bound to the fibers at less than 150° C. or without any external application of heat at ambient temperature (e.g., about 25° C.). Particles may also be bound in the absence of any external application of pressure, or in the absence of external heat and pressure.

In some embodiments the binder is associated with the fibers as a solid (for example, a dry powder or a dried liquid), and the fibers contain at least 7 percent water by weight when the binding step is performed. This level of moisture in the fibers provides sufficient mobility of reactants to allow the particles and fibers to bind well to each other. When a liquid binder is used (for example, glycerin or a solution of glycine powder), the fibers suitably contain at least about 0.5 percent water by weight. A solid binder is suitably used with fibers having 0.5 percent water by weight if the binder is heated above its melting point to liquefy it. A solid binder may be thermoplastic or meltable, such that it can be heated above its melting point and then cooled to fuse fibers to each other. The thermoplastic properties of the binder can also provide additional mechanical adherence between the particles and fibers. In some embodiments, a thermoplastic binder such as urea may be employed which can adhere particles both thermoplastically and with hydrogen bonding.

The invention also includes the products produced by any of the methods described herein.

The foregoing and other features and advantages of the invention will become more apparent from the following detailed description and accompanying drawings.

BRIEF DESCRIPTION OF THE DRAWINGS

FIG. 8 is a sectional view of the appliance of FIG. 9 taken along line 8—8 of FIG. 7.

FIG. 9 is a plan view of a disposable diaper including a core of fibers of the present invention.

DETAILED DESCRIPTION OF SEVERAL PREFERRED EMBODIMENTS OF THE INVENTION

Fiber Characteristics

Figure 1:
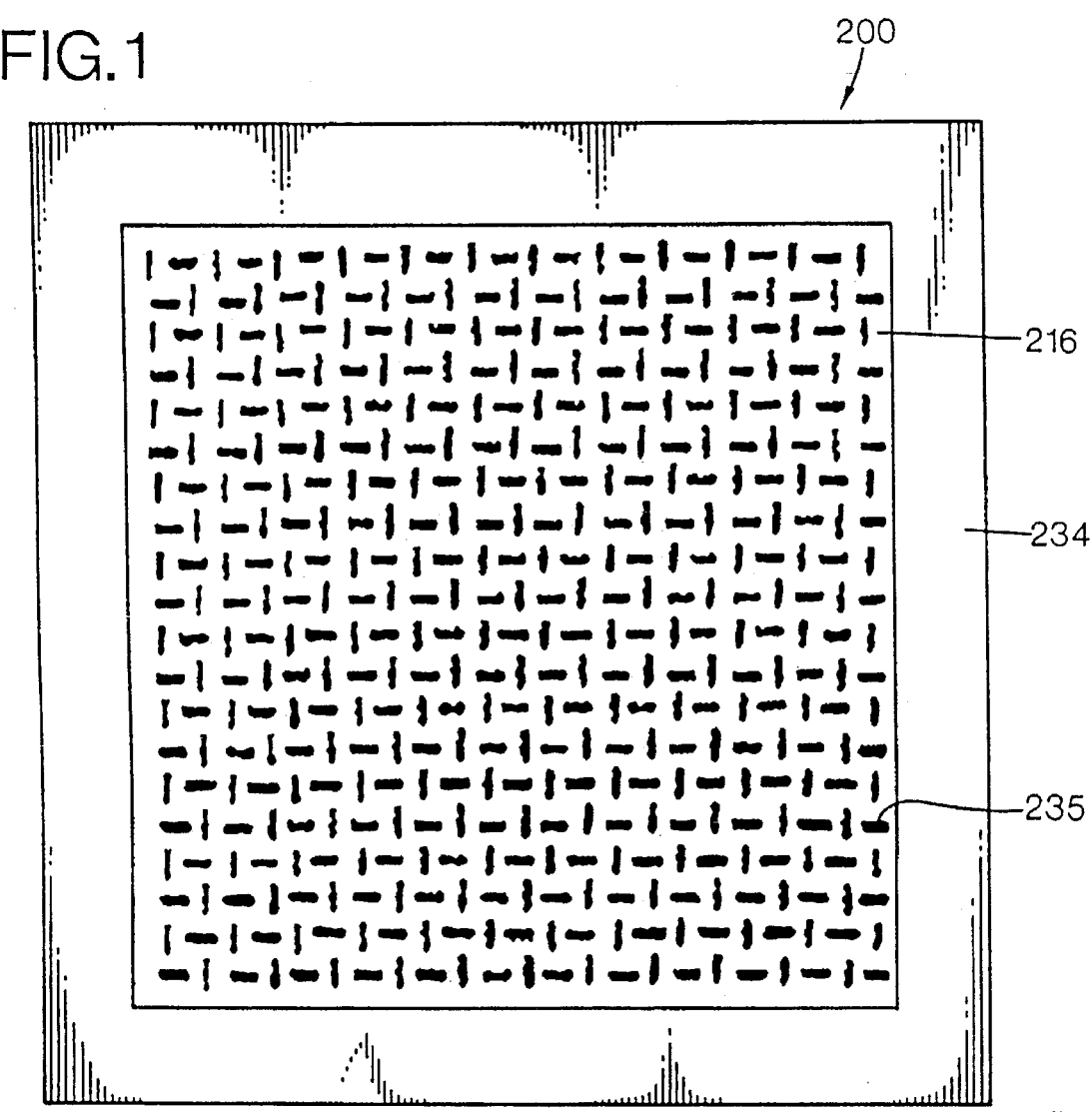
FIG. 1 is a top plan view of a structure into which fibers of the present invention are incorporated with attached particles, the fibers being in the form of an illustrated absorbent pad.

The present invention includes a method of binding particles to fibers, and the product produced by that method. In particularly preferred embodiments, the product is a cellulosic or synthetic fiber to which superabsorbent hydrogel polymer particles are adhered by a binder, and absorbent products made therefrom. Suitable fibers include wood pulp fibers, which can be obtained from well known chemical processes such as the kraft and sulfite processes. In these processes, the best starting material is prepared from long fiber coniferous wood species, such as pine, douglas fir, spruce and hemlock. Wood pulp fibers can also be obtained from mechanical processes, such as ground wood, mechanical, thermomechanical, chemimechanical, and chemithermomechanical pulp processes. The fibers are preferably elongated, for example having a length to width ratio of about 10:1 to 5:1.

The fibers of the present invention also include fibers that are pretreated prior to the application of a binder to the fibers as explained below. This pretreatment may include physical treatment, such as subjecting the fibers to steam or chemical treatment, such as cross-linking the fibers. Although not to be construed as a limitation, examples of pretreating fibers include the application of fire retardants to the fibers, such as by spraying the fibers with fire retardant chemicals. Specific fire retardant chemicals include, by way of example, sodium borate/boric acid, urea, urea/phosphates, etc. In addition, the fibers may be pretreated with surfactants or other liquids, such as water or solvents, which modify the surface of the fibers. Other pretreatments include exposure to antimicrobials or pigments.

The fibers may also be prepared in a way which increases their wettability. For example, natural fibers may be pretreated with a liquid sodium silicate, as by spraying the fibers with this material, for pretreatment purposes. Wettability of the surface of fibers is also improved by subjecting the fibers to a corona discharge pretreatment in which electrical current is discharged through the fibers in a conventional manner. In the case of both synthetic fibers and wood pulp fibers, corona discharge pretreatment results in an oxygen functionality on the surface of the fibers, making them more wettable and more bondable. The fibers may also be pretreated with conventional cross-linking materials and may be twisted or crimped, as desired. Pretreating cellulose fibers with chemicals which result in lignin or cellulose rich fiber surfaces may also be performed in a conventional manner.

Bleaching processes, such as chlorine or ozone/oxygen bleaching may also be used in pretreating the fibers. In addition, the fibers may be pretreated, as by slurrying the fibers in baths containing antimicrobial solutions (such as solutions of antimicrobial particles as set forth below), fertilizers and pesticides, and/or fragrances and flavors, for release over time during the life of the fibers. Fibers pretreated with other chemicals, such as thermoplastic and thermoset resins may also be used. Combinations of pretreatments may also be employed with the resulting pretreated fibers then being subjected to the application of the binder coating as explained below.

Ground wood fibers, recycled or secondary wood pulp fibers, and bleached and unbleached wood pulp fibers can be used. Details of the production of wood pulp fibers are well known to those skilled in the art. These fibers are commercially available from a number of companies, including Weyerhaeuser Company, the assignee of the present invention.

The fibers can also be any of a variety of other natural or synthetic fibers, however, all of the fibers to which particles are attached in accordance with the present invention include a hydrogen bonding functionality. This does not preclude the blending of such fibers with fibers lacking this characteristic. However, the fibers lacking a hydrogen bonding functionality will not have particles bonded thereto with the strength of the bonds that would be present if the fibers had a hydrogen bonding functionality.

A hydrogen bond is an intermolecular force that occurs between hydrogen atoms that are covalently bonded to small, strongly electronegative elements (such as nitrogen and oxygen) and nonbonding electron pairs on other such electronegative elements. A hydrogen bonding functionality is a functional group that contains an oxygen or nitrogen atom, for example hydroxyls, carboxyls, ethers, esters, epoxides, carbonyls, amines, urethanes and others, that is capable of forming a hydrogen bond. The orbitals of the nonbonding electron pairs on the oxygen or nitrogen overlap with the relatively empty 1s orbital of the hydrogen covalently bonded to another nitrogen or oxygen atom. The 1s orbital of the hydrogen is relatively empty due to the unequal sharing of the electrons in the covalent bond between it and the small electronegative atom (oxygen or nitrogen) to which it is bound.

Specific examples of natural fibers that contain a hydrogen bonding functionality include chopped silk fibers, wood pulp fibers, bagasse, hemp, jute, rice, wheat, bamboo, corn, sisal, cotton, flax, kenaf, peat moss, and mixtures thereof. Suitable synthetic fibers with hydrogen bonding functionalities include acrylic, polyester, carboxylated polyolefins, rayon and nylon. The hydrogen bonding functionality is an ester in acrylic fibers and a carboxylic acid in carboxylated polyolefin fibers, an ester in polyester, an amide in nylon, and a hydroxyl in rayon. Polyethylene and polypropylene would be unsuitable fibers for use in particle to fiber bonding in accordance with the present invention because they include only carbons and hydrogens without any oxygens or nitrogens that can participate in hydrogen bonds.

For purposes of convenience, and not to be construed as a limitation, the following description proceeds with reference to the treatment of individual chemical wood pulp fibers. The fibers are individualized, for example by defiberization in a hammermill. Such individualized fibers are conventionally formed into a mat, and are commercially available, for example as NB 416 from the Weyerhaeuser Company. Another suitable cellulosic mat would include Rayfloc JLD from ITT Rayonier. The cellulose fibers may be in the form of a cellulosic web or loose cellulose fibers.

Particle Characteristics

In accordance with the present invention, particles are added to the mat to give it desired properties, such as increased absorbency, abrasiveness, or antimicrobial activity. The particle can be any particulate material that has the desired property and which is capable of forming hydrogen bonds or coordinate covalent bonds with the binder. Hydrogen bonds can be formed, as discussed above, by particles that contain functional groups having an oxygen or nitrogen. Coordinate covalent bonds, in contrast, are formed by donation of a lone pair of electrons on one atom to an empty orbital of another atom. Coordinate covalent bonds differ from covalent bonds in that covalent bonds are formed by a pair of electrons wherein one of the electrons is donated from each of the atoms that participate in the bond. Particles can form coordinate covalent bonds if they have an empty p or d or f orbital that is capable of accepting a pair of electrons from the binder.

A coordinate covalent bond occurs between a donor compound that has a lone pair of electrons to donate to the bond, and an acceptor that has an empty orbital to accept the lone pair of electrons from the donor. According to the Aufbau and Pauli principles, electrons occupy the lobes of atomic orbitals one at a time with a maximum of two electrons (with opposite spins) per lobe. The most basic orbital is the s orbital, which is available for bonding the elements in the first row of the periodic table. In the second row of the periodic table, electrons fill first the 2s orbital of Li and Be, but metals in Groups IA and IIA do not have sufficient affinity for electrons to participate in coordinate covalent bonding. Beginning with column IIIA (boron), the three p orbitals participate in coordinate covalent bonding and the lobes of the p orbitals begin to fill. Boron has one electron in one of the 2p orbitals thus leaving the other two p orbitals empty and available for coordinate covalent bonding. An example of a coordinate covalently bonded boron containing particle is boric acid, which is used as an astringent, antiseptic and fire retardant. Boric acid is shown below wherein the boron is coordinate covalently bonded to a polypropylene glycol (PPG) binder.

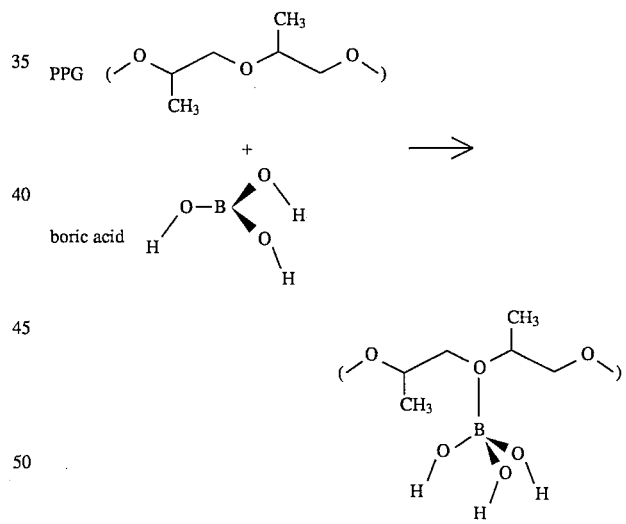

The next element, carbon, usually hybridizes to have one electron in the 2s orbital and the three remaining electrons are singly placed in the three p orbitals. This leaves no lobes empty for coordinate covalent bonding and electron additions proceeding further across that row of the periodic table also leave no lobes empty. Hence, boron is the only element in the second row of the periodic table that is capable of forming coordinate covalent bonds.

Next the third row begins to fill, and the two 3s electrons fill first in sodium and magnesium, but these metals in groups IA and IIA do not form coordinate covalent bonds as discussed above. Then aluminum, like boron, places one electron in one of the 3p lobes, and the two other 3p lobes are empty and available for coordinate covalent bonding.

The same trends continue across the third row, but the third row elements also have available five 3d lobes so the potential for coordination bonding exists even though 3p orbitals are occupied in the third row. Hence, Al, P, S, and Cl are capable of accepting a pair of electrons from an electron pair donor to form a coordinate covalent bond. An example of this is found in the bonding in PCl$_5$, aluminum trihydrate, or phosphorous pentasulfide. A phosphorous pentasulfide particle can be used to increase flammability of a product, while aluminum trihydrate is a fire retardant. An example of a coordinate covalently bonded aluminum compound is

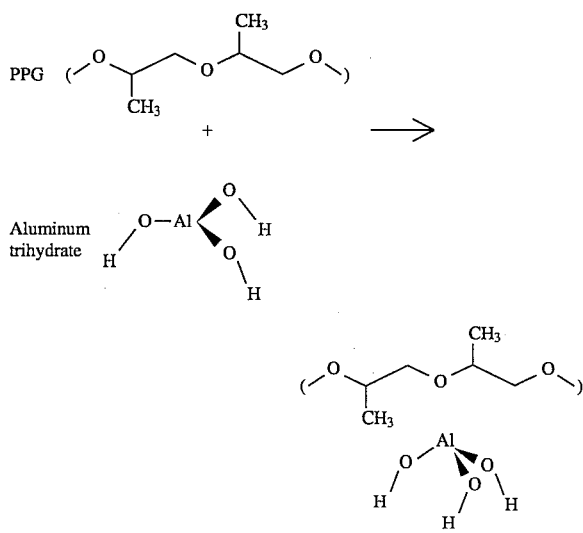

wherein aluminum trihydrate is coordinate covalently bonded to a polypropylene glycol (PPG) polymer.

In the next row, the 4s orbital is filled first, then the 3d lobes begin to fill—one electron per lobe until all have a single then a second electron to each lobe until all lobes are filled. However, 4p and 4f orbitals are also available, hence many of the transition elements are capable of forming coordinate covalent bonds.

The elements that have empty orbitals that participate in coordinate covalent bonding include all those except the metals (which excludes hydrogen) in groups IA and IIA, and C, N, O, F, Ne and He. Especially preferred particles contain boron, aluminum, iron, rhodium, osmium, platinum, and palladium, particularly boron. Examples of particles that are capable of coordinate covalent bonding are aluminum trihydrate, antimony oxide, arsenic disulfide, bismuth aluminate, bismuth iodide oxide, bismuth phosphate, bismuth subcarbonate, bismuth subgallate, cadmium salycilate, chromic carbonate, chromic hydroxide, chromic oxide, and chromic phosphate. All of the polymeric binders of the present invention (PPG, PAA, poly(caprolactone) diol, polyamide and polyamine) are capable of donating a lone pair of electrons from an oxygen or nitrogen to form a coordinate covalent bond with a suitable particle that has an empty orbital for coordinate covalent bonding.

Superabsorbent Particles

In one disclosed embodiment the added particles are superabsorbent particles, which comprise polymers that swell on exposure to water and form a hydrated gel (hydrogel) by absorbing large amounts of water. Superabsorbents are defined herein as materials that exhibit the ability to absorb large quantities of liquid, i.e. in excess of 10 to 15 parts of liquid per part thereof. These superabsorbent materials generally fall into three classes, namely starch graft copolymers, crosslinked carboxymethylcellulose derivatives and modified hydrophilic polyacrylates. Examples of such absorbent polymers are hydrolyzed starch-acrylonitrile graft copolymer, a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-crosslinking polyacrylic acid, a crosslinked polyacrylate salt, carboxylated cellulose, and a neutralized crosslinked isobutylene-maleic anhydride copolymer.

Superabsorbent particles are available commercially, for example starch graft polyacrylate hydrogel fines (IM 1000F) from Hoechst-Celanese of Portsmouth, Va., or larger particles such as granules. Other superabsorbent particles are marketed under the trademarks SANWET (supplied by Sanyo Kasei Kogyo Kabushiki Kaisha), SUMIKA GEL (supplied by Sumitomo Kagaku Kabushiki Kaisha and which is emulsion polymerized and spherical as opposed to solution polymerized ground particles), FAVOR (supplied by Stockhausen of Greensboro, N.C.), and NORSOCRYL (supplied by Atochem). The superabsorbent particles come in a variety of sizes and morphologies, for example IM 1000 and IM 1000F. The 1000F is finer and will pass through a 200 mesh screen whereas IM 1000 has particles that will not pass through a 60 mesh screen. Another type of superabsorbent particle is IM 5600 (agglomerated fines). Superabsorbent particulate hydrophilic polymers are also described in detail in U.S. Pat. No. 4,102,340, which is incorporated herein by reference. That incorporated patent discloses hydrocolloid absorbent materials such as cross-linked polyacrylamides.

Other Particles

Many particles that form hydrogen bonds or coordinate covalent bonds are suitable for use with the present invention. Some such particles are listed in Table 1 with an indication of the function of the listed particles.

TABLE I

| Particulates For Binding | |
|---|---|
| Name | Function |
| Aluminum Trihydrate | Fire retardant, astringent |
| Acediasulfone | Antibacterial |
| Agaricic acid | Antiperspirant |
| Alclometastone | Topical anti-inflammatory |
| Calcium alginate | Topical hemostatic |
| Amidomycin | Fungicide |
| Antimony oxide | Fire retardant |
| Apigenin | Yellow dye, mordant |
| Arsenic disulfide | Red Pigment |
| Aspirin | Anti-inflammatory; antipyretic |
| Azanidazole | Antiprotozoal (Trichomonas) |
| Azelaic acid | Antiacne |
| Baicalein | Astringent |
| Bendazac | Anti-inflammatory |
| Benomyl | Fungicide; ascaricide |
| Benzestrol | Estrogen |
| Benzylpenicillinic acid | Antibacterial |
| Benzylsulfamide | Antibacterial |
| Bergaptene | Antipsoriatic |
| Betasine | Iodine source |
| Bezitramide | Narcotic analgesic |
| Bibrocathol | Topical antiseptic |
| Bietanautine | Antihistaminic |

TABLE I-continued

Particulates For Binding

| Name | Function |
|---|---|
| Bifenox | Herbicide |
| Bifonazole | Antifungal |
| Binapacryl | Fungicide, miticide |
| Bis(p-chlorophenoxy) methane | Miticide |
| Bismuth aluminate | Antacid |
| Bismuth iodide oxide | Anti-infective |
| Bismuth phosphate | Antacid; protectant |
| Bismuth subcarbonate | Topical protectant |
| Bismuth subgallate | Astringent, antacid; protectant |
| Bisphenol A | Fungicide |
| Bitertanol | Agricultural fungicide |
| Bithionol | Topical anti-infective |
| Bromacil | Herbicide |
| Bromadiolone | Rodenticide |
| Bromcresol green | Indicator |
| Bromcresol purple | Indicator |
| Bromethalin | Rodenticide |
| p-Bromoacetanilide | Analgesic; antipyretic |
| 3-Bromo-d-camphor | Topical counterirritant |
| Bromophos | Insecticide |
| Bromopropylate | Acaricide |
| 5-Bromosalicyl-hydroxamic acid | antibacterial (tuberculostatic) |
| 5-Bromosalycilic acid acetate | Analgesic |
| Bromosaligenin | Anti-inflammatory |
| Bromthymol blue | Indicator |
| Broxyquinoline | Antiseptic; disinfectant |
| Bucetin | Analgesic |
| Bumadizon | Analgesic; anti-inflammatory; antipyretic |
| Bupirimate | Fungicide |
| Busulfan | Carcinogen, insect sterilant, antineoplastic |
| Butamben | Topical anesthetic |
| Butrylin | Insecticide |
| Butylated hydroxy-anisole | Antioxidant (BRA) |
| Butyl paraben | Pharmaceutic aid; food preservative |
| 4-tert-Butylphenyl salicylate | Light absorber |
| Cacotheline | Indicator |
| Cactinomycin | Antineoplastic |
| Cadmium salycilate | Antiseptic |
| Calamine | Skin protectant |
| Calcium carbonate | Antacid |
| Calcium saccharate | Pharmaceutic aid |
| Calcium tartrate | Preservative; deodorant; antacid |
| Cambendazole | Anthelminthic |
| Candicidin | Topical antifungal |
| Candidin | Topical antifungal |
| Capsaicin | Topical analgesic |
| Captan | Fungicide; bacteriostat |
| Carbadox | Antimicrobial |
| Carbamazepine | Anticonvulsant; analgesic |
| Carbarsone | Antiamebic |
| Carbaryl | Contact insecticide |
| Carbazochrome salycilate | Antihemorrhagic |
| Carbendazim | Fungicide |
| Carbochloral | Hypnotic |
| Carbophenothion | Miticide; insecticide |
| Carboquone | Antineoplastic |
| Carisoprodol | Skeletal muscle relaxant |
| Carthamin | Dye |
| Carvacrol | Disinfectant |
| Cephalin | Local hemostatic |
| Chalcomycin | Antibiotic |
| Chartrausin | Antibiotic |
| Chitin | Vulnerary |
| Chloramben | Herbicide |
| Chloramphenacol palmitate | Antimicrobial |
| Chloranil | Fungicide |
| Chlorbetamide | Antiamebic |
| Chlordimeform | Insecticide |
| Chlorfenac | Herbicide |
| Chlorfenethol | Acaricide |
| Chlorhexidine | Topical antibacterial |
| Chloroazodin | Antibacterial; topical anesthetic |
| Chlorophacinone | Anticoagulant rodenticide |
| p-Chlorophenol | Antiseptic |
| Chlorothricin | Antibiotic |
| Chlorotrianisene | Estrogen |
| Chloroxylanol | Antiseptic; germicide |
| Chlorphenesin | Topical antifungal |
| Chlorphenesin carbamate | Relaxant (skeletal muscle) |
| Chlorphenoxamide | Antiamebic |
| Chlorpropamide | Antidiabetic |
| Chlorpyrifos | Insecticide |
| Chlorquinaldol | Topical antibacterial |
| Chlorsulfuron | Herbicide |
| Chlorothion | Insecticide |
| Chlozoxazone | Relaxant |
| Cholesterol | Pharmaceutic aid |
| Chromic carbonate | Pigment |
| Chromic hydroxide | Pigment |
| Chromic oxide | Abrasive |
| Chromic phosphate | Green pigment |
| Chrysamminic acid | Explosive |
| Chrysarobin | Antipsoriatic |
| Cilastazol | Antithrombotic |
| Cinoxate | Sunscreen agent |

Other suitable particles include proteins, vitamins, zeolites and silica, which contain oxygen or nitrogen groups, or both. An example of a suitable zeolite is Abscents odor absorber available from UOP of Tarrytown, N.Y. An example of a suitable antimicrobial particle is chlorhexidine (N,N"-Bis(4-chlorophenyl)-3,12-diimino-2,4,11,13-tetraazatetradecane-diimidamide). The list in Table I is by no means exhaustive as it can be readily determined for each type of particle whether it is capable of forming a hydrogen bond or a coordinate covalent bond. Many of the particles are non-absorbent, or not superabsorbent polymers.

The particles listed in Table 1 have chemical properties that make them suitable for binding to fibers with the binders of the present invention. The listed particles are organic or inorganic compounds that have little or no water solubility, yet have the capacity to hydrogen bond. Water solubility is preferably low, for example, less than 10 g dissolves completely in 300 ml of water at 25° C., more preferably less than about 1 g in 300 ml at 25° C. This low solubility allows the particles to remain solid, and the hydrogen bonding capacity allows them to adhere to the fibers. Once bound, the particles substantially retain a discrete particulate form instead of dissolving or fusing. More of the particles are discrete than fused once bound.

The amount of binder added to the fibers can vary widely, for example from 0.05 to 80 percent of the total weight of the fibrous material, binders and particles. Antimicrobials such as chlorhexidine are effective in very low amounts, such as 0.05 percent. Superabsorbent particles are preferably added in an amount of 3–40 percent, especially 15–25 percent by weight.

Polymeric Binder Characteristics

The particles may be bound to the fibers by a water soluble polymeric binder selected from a predetermined group of polymeric binders that each have a hydrogen bonding functionality or coordinate covalent bond forming functionality on each repeating unit of the polymer. In accordance with the present invention, the predetermined groups of polymeric binders includes the set of binders consisting of polypropylene glycol (PPG); a copolymer; polyacrylic acid; a poly(caprolactone) diol; a polyamide such as polyglycine or another polypeptide; or a polyamine such as polyethyleneimine or polyvinyl pyridine. As used herein, a polymer is a macromolecule formed by chemical union of 5 or more identical combining units (monomers). A polyamine is a polymer that contains amine functional groups and a polyamide is a polymer that contains amide functional groups. Each of the binders has a hydrogen bonding or a coordinate covalent bonding functionality on each repeating unit (monomer) of the polymer. This repeating functionality may be a hydroxyl, carboxylic acid, amide, ether or amine. These binders are capable of forming hydrogen bonds because they have a functional group that contains an oxygen or a nitrogen.

The polyglycol has repeating ether units with hydroxyl groups at the terminal ends of the molecule, and polyacrylic acid has a repeating carboxyl group in which a hydrogen is bound to an electronegative oxygen, creating a dipole that leaves the hydrogen partially positively charged. The polyamide (such as a polypeptide) or polyamine has a repeating NR group in which a hydrogen may be bound to an electronegative nitrogen that also leaves the hydrogen partially positively charged. The hydrogen in both cases can then interact with an oxygen or nitrogen on the particle or fiber to form a hydrogen bond that adheres the binder to the particle and fiber. The electronegative oxygen or nitrogen of the binder can also form a hydrogen bond with hydrogens on the particle or fiber that have positive dipoles induced by oxygens or nitrogens to which the hydrogen is attached. The polyamide also has a carboxyl group with an electronegative oxygen that can interact with hydrogen atoms in the particles or fibers.

Thus, the polymeric binders enhance the hydrogen bonding (a) between the fibers and binder; and (b) in the case of particles with hydrogen bonding functionalities, between the binder and the particles.

Alternatively, the polymeric binder may form a coordinate covalent bond with the particles and a hydrogen bond to the fibers. For example, the oxygen or nitrogen on the binder has an unbound pair of electrons that can be donated to an empty orbital in the particle to form a coordinate covalent bond. For example, one free pair of electrons on the oxygen or nitrogen can be donated to the empty p orbital of a boron containing particle to form a coordinate covalent bond that adheres the particle to the binder. The fibers themselves contain functional groups that can form hydrogen bonds with the binder, and allow the binder to adhere to the fiber. Cellulosic and synthetic fibers, for example, contain hydroxyl, carboxyl, amide, ether and ester groups that will hydrogen bond with the hydroxyl, carboxylic acid, amide or amine groups of the binder. Hence the polymeric binder will adhere the particle with a coordinate covalent bond and the fiber will adhere with a hydrogen bond.

In some preferred embodiments, the polymeric binder is bound to both the fibers and the particle by hydrogen bonds. A polypropylene glycol binder, for example, can be used to bind polyacrylate hydrogel particles to cellulosic fibers. The hydroxyl and ether groups on the glycol binder participate in hydrogen bonding interactions with the hydroxyl groups on the cellulose fibers and the carboxyl groups on the polyacrylate hydrogel, as shown below:

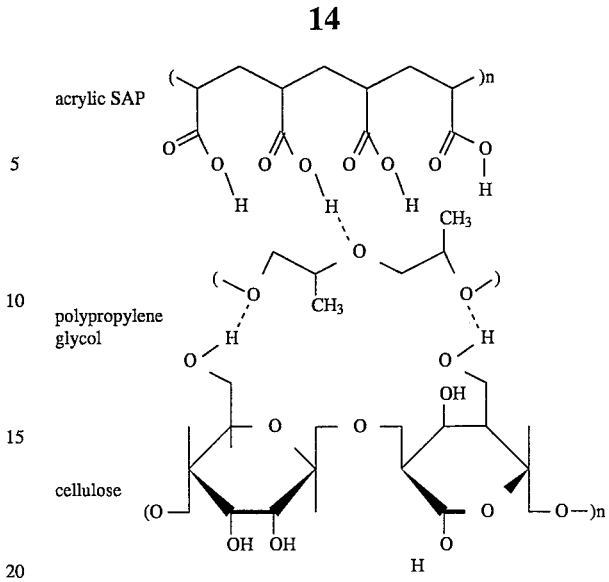

Hence the binder will adhere both the particle and fiber with hydrogen bonds. The presence of a hydrogen bonding functionality on each repeating unit of the polymeric binder has been found to increase the number of hydrogen bonding interactions per unit mass of polymer, which provides superior binding efficiency and diminishes separation of particles from the fibers. The repeating ether functionality on the glycol binder provides this efficiency in the example diagrammed above. A repeating carboxyl group is the repeating functionality on polyacrylic acid, while repeating carbonyls and NR groups (wherein R is either an H or alkyl, preferably lower alkyl i.e. less than five carbon atoms, with the alkyl normal or iso) of the amide linkages are the repeating functionalities on polyamides such as polypeptides. A repeating amine group is present on polyamines.

The polymeric organic binders of the present invention have been found to increase in binding efficiency as the length of the polymer increases, at least within the ranges of molecular weights that are reported in the examples below. This increase in binding efficiency is attributable to the increased number of hydrogen bonding or coordinate covalent bonding groups on the polymer with increasing molecular length. Each of the polymeric binders has a hydrogen bonding or coordinate covalent bonding functionality on each repeating unit of the polymer, hence longer polymers provide more hydrogen bonding groups or coordinate covalent bonding groups that can participate in hydrogen bonding interactions or coordinate covalent bonds.

Although the invention is not limited to polymeric binders of particular molecular weights, polymeric binders having a molecular weight greater than 500 grams/mole are preferred because they provide attractive physical properties, and the solid is less volatile and more thermoplastic as compared to small polymeric binders. Polymeric binders with molecular weights greater than 4000 grams/mole are especially preferred, because they have minimal volatility and are less likely to evaporate from the fibers. In some particular embodiments, polymers with molecular weights between 4000 and 8000 grams/mole have been used. Polymers with molecular weights above 8000 may be used, but exceedingly high molecular weight polymers may decrease binding efficiency because of processing difficulties.

Certain polymeric binders have greater binding efficiency because their repeating functionality is a more efficient hydrogen bonding group. It has been found that repeating amide groups are more efficient than repeating carboxyl functionalities, which are more efficient than repeating hydroxyl functionalities, which in turn are more efficient than amine or ether functionalities. Hence, polymeric binders may be preferred that have repeating amine or ether functionalities, more preferably repeating hydroxyl functionalities, and even more preferably repeating carbonyl or carboxyl functionalities, and most preferably repeating amide functionalities. Binding may occur at any pH, but is suitably performed at a neutral pH of 5–8, preferably 6–8, to diminish acid hydrolysis of the resulting fibrous product. Suitable binders may be selected from the group consisting of polyethylene glycol; polyethylene glycol and polypropylene glycol, including copolymers thereof; polyethylene glycol, polypropylene glycol and polyacrylic acid; polyethylene glycol, polypropylene glycol, polyacrylic acid, and a polyamide; polyethylene glycol, polypropylene glycol, polyacrylic acid, a polyamide and a polyamine; polypropylene glycol alone; polypropylene glycol and polyacrylic acid; polypropylene glycol alone; polypropylene glycol, polyacrylic acid and a polyamide; and polypropylene glycol, polyacrylic acid, a polyamide and a polyamine; polyacrylic acid alone; polyacrylic acid and a polyamide; polyacrylic acid, a polyamide and a polyamine; a polyamide alone; a polyamide and a polyamine; or a polyamine alone. Poly(caprolactone) diol may optionally be a member of any of these groups.

The group consisting of polyacrylic acid, polyamide and polyamine has been found to have a especially good binding efficiency. Among polyamides, polypeptides are especially preferred.

Non-Polymeric Binder Characteristics

The particles may be bound to the fibers by a non-polymeric organic binder selected from a predetermined group of binders that each have a volatility less than water. The vapor pressure of the binder may, for example, be less than 10 mm Hg at 25° C., and more preferably less than 1 mm Hg at 25° C. The non-polymeric binder has a functional group that forms hydrogen bonds or coordinate covalent bonds with the particles. In accordance with the present invention, the predetermined group of non-polymeric binders may include a functionality such as an alcohol, a carboxylic acid, an aldehyde, an amino acid, an amide, or an amine, wherein each binder includes at least two such functionalities, and the two functionalities are the same or different. A requirement for the non-polymeric binder is that it have a plurality of functional groups capable of hydrogen bonding, or at least one group that can hydrogen bond and at least one group that can form coordinate covalent bonds. As used herein, the term "non-polymeric" refers to a monomer, dimer, trimer, tetramet, and oligomers, although some particular non-polymeric binders are monomeric and dimeric, preferably monomeric.

Particularly preferred non-polymeric organic binders can form five or six membered rings with a functional group on the particle surface. An example of such a binder is an amine or amino acid (for example, a primary amine or an amino acid such as glycine) which forms six membered rings by forming hydrogen bonds:

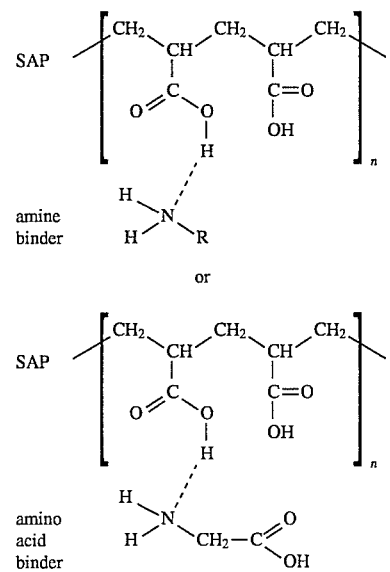

A six membered ring is also formed by the hydroxyl groups of carboxylic acids, alcohols, and amino acids.

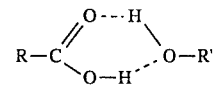

A five membered ring can be formed by the binder and the functionality on the surface of the particle, for example

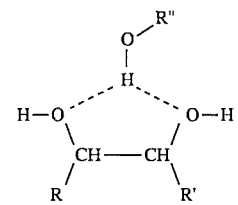

wherein the particle is SAP and the binder is an alcohol, such as a polyol with hydroxyl groups on adjacent carbons, for example 2,3-butanediol.

other alcohols that do not form a five membered ring can also be used, for example alcohols that do not have hydroxyl groups on adjacent carbons. Examples of suitable alcohols include primary, secondary or tertiary alcohols.

Amino alcohol binders are alcohols that contain an amino group (—NR$_2$), and include binders such as ethanolamine (2-aminoethanol), diglycolamine (2-(2-aminoethoxy)ethanol)). Non-polymeric polycarboxylic acids contain more than one carboxylic acid functional group, and include such binders as citric acid, propane tricarboxylic acid, maleic acid, butanetetracarboxylic acid, cyclopentanetetracarboxylic acid, benzene tetracarboxylic acid and tartaric acid. A polyol is an alcohol that contains a plurality of hydroxyl groups, and includes diols such as the glycols (dihydric alcohols) ethylene glycol, propylene glycol and trimethylene glycol; triols such as glycerin (1,2,3-propanetriol); and polyhydroxy or polycarboxylic acid compounds such as tartaric acid or ascorbic acid (vitamin C):

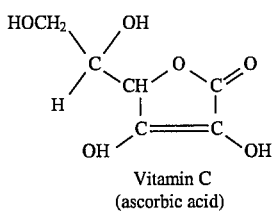

Vitamin C
(ascorbic acid)

Hydroxy acid binders are acids that contain a hydroxyl group, and include hydroxyacetic acid ($CH_2OHCOOH$) and lactic, tartaric, ascorbic, citric, and salicylic acid. Amino acid binders include any amino acid, such as glycine, alanins, valine, setins, threonine, cysteine, glutamic acid, lysine, or β alanine. Non-polymeric polyamide binders are small molecules (for example, monomers or dimers) that have more than one amide group, such as oxamide, urea and biuret. Similarly, a non-polymeric polyamine binder is a non-polymeric molecule that has more than one amino group, such as ethylene diamine, EDTA or the amino acids asparagine and glutamine.

Each of the non-polymeric binders disclosed above is capable of forming hydrogen bends because it has a functional group that contains an oxygen or nitrogen, or has oxygen or nitrogen containing groups that include a hydrogen. The amino alcohol, amino acid, carboxylic acid, alcohol and hydroxy acid all have a hydroxyl group in which a hydrogen is bound to an electronegative oxygen, creating a dipole that leaves the hydrogen partially positively charged. The amino alcohol, amino acid, amide and amine all have an NR group in which a hydrogen may be bound to an electronegative nitrogen that also leaves the hydrogen partially positively charged. The partially positively charged hydrogen in both cases then can interact with an oxygen or nitrogen on the particle or fiber that adheres the binder to the particle and fiber. The polycarboxylic acid, hydroxy acid, amino acid and amide also have a carboxyl group with an electronegative oxygen that can interact with hydrogen atoms in the particles and fibers. Similarly, electronegative atoms (such as oxygen or nitrogen) on the fiber or particle can interact with hydrogen atoms on the binder that have positive dipoles, and partially positive hydrogen atoms on the fiber or particle can interact with electronegative atoms on the binder.

Several hydrogen bonding interactions of two of the binders (glycine and 1,3-propanediol) with cellulose are shown below:

The hydrogen bonding interactions are shown as dotted lines. One such interaction is shown between the nitrogen of glycine and a hydrogen of an OH on cellulose. A hydrogen bond with glycine is also shown between an oxygen of the OR on glycine and the hydroxy hydrogen of an alcohol sidechain on cellulose. Hydrogen bonding interactions of the 1,3-propanediol are shown in dotted lines between an oxygen on an OH group of the binder and a hydrogen of an OH group on the cellulose molecule. Another hydrogen bond is also shown between a hydrogen on an OH group of the glycol binder and an oxygen in an alcohol sidechain of the cellulose.

Alternatively, the oxygen or nitrogen on the binder has an unbound pair of electrons that can be donated to an empty orbital in the particle to form a coordinate covalent bond. The free pair of electrons on the oxygen or nitrogen can be donated to the empty p, d or f orbital of a particle (for example a boron containing particle) to form a coordinate covalent bond that adheres the particle to the binder. The fibers themselves do not normally contain functional groups that can form coordinate covalent bonds with the binders, but hydrogen bonding interactions allow the binder to adhere to the fiber. Cellulosic and synthetic fibers, for example, contain hydroxyl, carboxyl and ester groups that will hydrogen bond with the hydroxyl, carboxylic acid, amide or amine groups of the binder. Non-cellulosic or non-synthetic fibers that have these functionalities can also be used, for example silk, which has an amide linkage. Hence the binder will adhere the particle with a coordinate covalent bond and the fiber with a hydrogen bond.

In some preferred embodiments, the binder is bound to both the fibers and the particle by hydrogen bonds. A polyol binder, for example, can be used to bind polyacrylate hydrogel particles to cellulosic fibers. The hydroxyl groups on the polyol binder participate in hydrogen bonding interactions with the hydroxyl groups on the cellulose fibers and the carboxyl groups on the polyacrylate hydrogel. Hence the binder will adhere both the particle and fiber with hydrogen bonds. These hydrogen bonds provide excellent binding efficiency and diminish separation of bound particles from the fibers.

A structural drawing is shown below in which citric acid, vitamin C and urea adhere polyacrylate particles to cellulose with hydrogen bonds. Some of the possible hydrogen bonding interactions are shown as dashed lines.

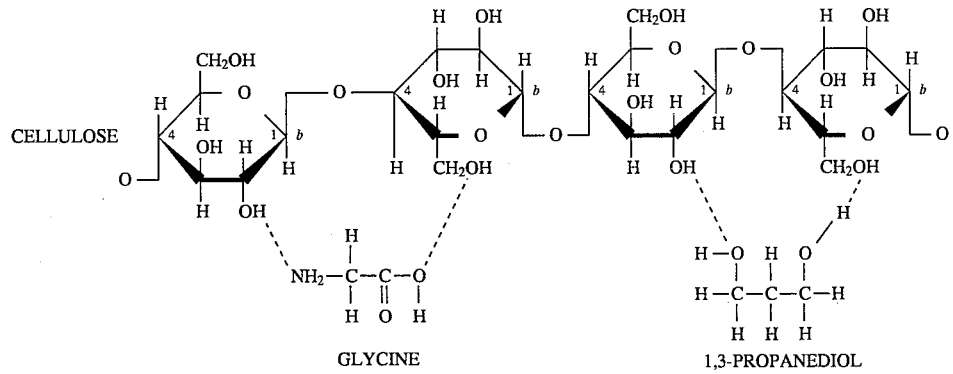

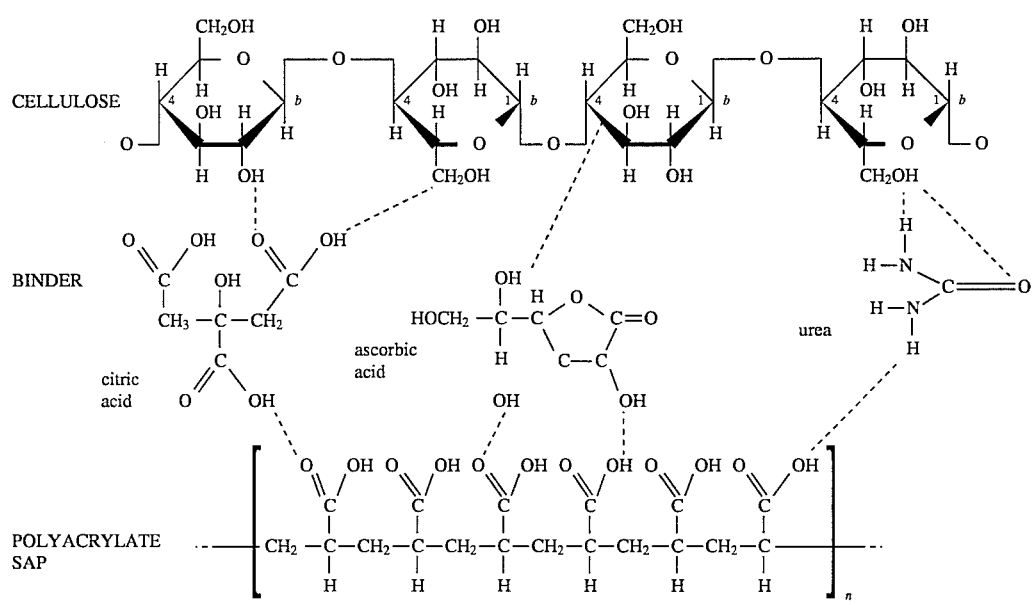

Particularly efficient hydrogen bonding binders include those with carboxyl groups, such as ascorbic acid, or amide groups, such as urea. Hydroxyl groups are also very efficient binders. Amine and ether functionalities are less efficient binders.

Binders have functional groups that may be selected independently or in combination from the group consisting of a carboxylic acid, an alcohol, an amide and an amine, wherein the binder has at least two of these functional groups, and each of the functional groups can be the same (for example, a polyol, polycarboxylic acid, glyoxal, and polyamine or polyamide) or different (for example, an amimo alcohol, hydroxyamide, carboxyamide, or amino acid). Functional groups may also be selected independently or in combination from the group consisting of a carboxylic acid alone; a carboxylic acid and an alcohol; a carboxylic acid, an alcohol and an amide; a carboxylic acid, an alcohol, an amide and an amine; an alcohol alone; an alcohol and an amide; an alcohol, an amide and an amine; an amide alone; an amide and an amine; and an amine alone. An aldehyde may optionally be a member of any of these groups.

Preferred functional groups for the non-polymeric binders may be selected independently or in combination from the group consisting of an amino alcohol, a polycarboxylic acid, a polyol, a hydroxy acid, an amino acid, an amide, and a polyamine. Other preferred groups of binders include an amino alcohol alone, an amino alcohol and a polycarboxylic acid, an amino alcohol, a polycarboxylic acid and a polyol; an amino alcohol, a polycarboxylic acid, a polyol and a hydroxy acid; an amino alcohol, a polycarboxylic acid, a polyol, a hydroxy acid and an amino acid; an amino alcohol, a polycarboxylic acid, a polyol, a hydroxy acid, an amino acid and an amide; a polycarboxylic acid and a polyol; a polycarboxylic acid, a polyol and a hydroxy acid; a polycarboxylic acid, a polyol, a hydroxy acid, and an amino acid; a polycarboxylic acid, a polyol, a hydroxy acid, an amino acid and an amide; a polycarboxylic acid, a polyol, a hydroxy acid, an amino acid, an amide and a polyamine; a hydroxy acid and an amino acid; a hydroxy acid, amino acid and amide; a hydroxy acid, amino acid, amide and polyamine; an amino acid and an amide; an amino acid, amide and a polyamine; an amide and a polyamine; an amino alcohol alone, a polycarboxylic acid alone, a polyol alone, a hydroxy acid alone, an amino acid alone, an amide alone and a polyamine alone.

More specifically, the functionalities of the non-polymeric binder may be selected from the group of glycerin (a polyol), ascorbic acid (a polycarboxylic acid and a hydroxy acid), glyoxal (a polyaldehyde), urea (a polyamide), glycine (an amino acid), pentaerythritol (a polyol), a monosaccharide, a disaccharide (a polyhydric alcohol), as well as citric acid, tartaric acid, dipropylene glycol, and urea derivatives such as DMDHEU. Subgroupings include glycerin; glycerin and ascorbic acid; glycerin, ascorbic acid and urea; glycerin, ascorbic acid, urea and glycine; glycerin, ascorbic acid, urea, glycine and pentaerythritol; glycine, ascorbic acid, urea, glycine, pentaerythritol and a monosaccharide; glycerin, ascorbic acid, urea, glycine, pentaerythritol, a monosaccharide and a disaccharide; ascorbic acid; ascorbic acid and urea; ascorbic acid, urea and glycine; ascorbic acid, urea, glycine and pentaerythritol; ascorbic acid, urea, glycine, pentaerythritol and a monosaccharide; ascorbic acid, urea, glycine, pentaerythritol, monosaccharide and a disaccharide; urea; urea and glycine; urea, glycine and pentaerythritol; urea, glycine, pentaerythritol and a monosaccharide; urea, glycine, pentaerythritol, a monosaccharide and a disaccharide; glycine; glycine and pentaerythritol; glycine, pentaerythritol and a monosaccharide; glycine, pentaerythritol, a monosaccharide and a disaccharide; pentaerythritol; pentaerythritol and a monosaccharide; pentaerythritol, a monosaccharide and a disaccharide; a monosaccharide; a monosaccharide and a disaccharide; and a disaccharide.

Process Advantages

The binders of the present invention also provide numerous process advantages. Binding of particles to the fibers can occur, for example, without external application of heat. Hence particle binding may occur at ambient temperature if desired. The present invention is therefore distinct from prior art crosslinking processes in which elevated temperatures are required to covalently crosslink cellulose groups to one another. Moreover, the binders of the present invention have the advantage of being reactivatable by addition of a liquid solvent such as water. Hence, a liquid binder (which would include a solution of a solid or liquid binder, or a binder that has a melting point below room temperature) can be applied to a cellulose mat in the absence of the particles to be bound and the binder allowed to air dry, for example until it reaches an equilibrium moisture content with the moisture in the ambient air. Alternatively, the binder can be applied as a solid, for example as particles or a powder. At a later stage of processing, water or another liquid is added to those portions of the mat where particulate binding is desired. The particles may then be added to the mat and adhered to those portions of the mat that have been moistened. Alternatively, the particles may be added to the mat prior to activation of the binder.

The binders may be liquids at room temperature (such as glycerin), or liquid solutions of binders that are solids at room temperature (for example, an aqueous solution of glycine), or liquid hot melts of solid binders. Solid binders may be added to fibers in particulate form, for example, by sprinkling binder particles on the fibers.

The binding reaction of the present invention can occur across a broad range of pH without requiring a catalyst. A suitable pH range without a catalyst is 1–14, but preferred ranges are 5–8 or 6–8 because such neutral pH ranges will produce fibrous products (such as cellulose products) that are less prone to damage by acid hydrolysis.

The moisture content of the fibers during the binding reaction is 0.5–50%, suitably 5–40%, or preferably 5–20% water by weight of the fibers, binder and particle. A moisture content greater than 20%, preferably greater than 30%, or in the range 20–50%, or 30–50%, can be used even though such high moisture contents would interfere with intermediate anhydride formation and inhibit formation of covalent bonds in the production of high bulk fibers. Particles may be added to the fibers such that the particles are distributed throughout a fibrous product without being confined to a surface of the product. The particles can be distributed throughout the depth of a fiber product such as a mat or web.

The binder is suitably present in the treated product in an amount of at least 3 percent and no more than 80 percent by weight of the fibers, particles, and binder ("percent by weight"). In especially preferred embodiments, the binder is present in an amount of 5–30 percent by weight. Below about 3 percent, an insufficient amount of binder is present to achieve adequate binding, while using excessive amounts of binder can introduce unnecessary expense into the binding process. High percentages of binder can also cause processing problems because the binder material transfers to equipment surfaces.

Thermoplastic binders may also be used to help bind fibers to each other and particles to fibers. The binder that has the hydrogen bonding or coordinate covalent bonding functionalities may itself be thermoplastic. The polymeric binders of the present invention have the advantage of being thermoplastic solids. Hence fibers treated in accordance with the present invention can be thermobonded by elevating the fiber temperature above the melting temperature of the binder to melt the thermoplastic binder and thermoplastically bind the fibers to each other and the fibers to the particles. Alternatively, an auxiliary or second binder can be applied to the fibers as a solid at room temperature, and the temperature of the second binder elevated above its melting point to thermobond the fibers and particles. The auxiliary binder may be applied to the fibers either before or after the primary binder is applied, but before thermobonding.

The binders of the present invention may be used with fibers that have substantial intrafiber covalent crosslinks (such as HBA available from Weyerhaeuser) or fibers which are substantially free of infrafiber covalent crosslinking. Examples of individualized intrafiber crosslinked fibers are seen in European Patent Applications 440 472 A1 and 427 317 A2, which produce products that those publications describe as being substantially free of interfiber bonds. Those fibers have been individualized and then cured in the presence of a crosslinking material at an elevated temperature to produce high bulk fibers having intrafiber covalent crosslinks. The fibers of the present invention do not need to be processed as in those European applications to eliminate interfiber bonds. Binders of the present invention can therefore be used with natural fibers that have substantial interfiber bonding, which is defined as fibers that have not been processed as in European Applications 440 472 A1 and 427 317 A2 to substantially eliminate interfiber bonds. Cellulose fibers that have not been so processed are substantially free of intrafiber bonds.

Although intrafiber covalent crosslinking is not required for the present invention, such high bulk fibers can be used with the binders disclosed herein. Fibers that have high bulk from intrafiber covalent crosslinks are prepared by individualizing the fibers and curing them at an elevated temperature (above 150° C.) in the presence of a crosslinking material such as citric acid. Initial application of the binder on such high bulk fibers may occur after the curing step, particularly if the binder is capable of functioning as a crosslinking material. The binders disclosed herein that can also crosslink are polyols, polycarboxylic acids, and polyamines (both polymeric and non-polymeric binders that have more than one amine group); none of the other specifically disclosed binders are known to form covalent, intrafiber bonds. If crosslinking binders are present during curing, the binder can be consumed during the curing step to form covalently crosslinked ester bonds. When this occurs, the binder is no longer available for hydrogen bonding, and particle binding to fibers is ineffective.

The binder can be applied before curing, even if the binder is also a crosslinking material. If the binder is a crosslinking material, steps are taken to inhibit formation of anhydride intermediates that are required for covalent bond formation. Anhydride formation can be inhibited, for example, by adding a sufficient amount of water to the fibers to inhibit anhydride formation without preventing all covalent crosslinking from occurring. Inhibition of anhydride formation can occur when the fibers have 20% water by weight of the fiber and are cured at 150° C. for 20 minutes. Hence, at least 20% water (preferably 30%) by weight of the fiber should be present, or 20–50% water. Higher amounts of water within this range are preferred when curing at temperatures higher than 150° C., or for periods of time longer than 20 minutes.

The fibrous product of the present method (with or without intrafiber crosslinking) may further be densified by external application of pressure. The densified product is compact, easily transported, and has superior absorbent properties as compared to non-densified products. The present inventors have found that the binders of the present invention produce a product that can be easily densified. Easy densification is associated with the hydrogen bonds and coordinate covalent bonds formed between the binder and the particles and fibers. The fibers are particularly easily densified when at least 5% by weight of the fibers, particles, and binder, more preferably 10%, are particles adhered to the fibers by the hydrogen bonds and/or coordinate covalent bonds of the present invention.

In accordance with this invention, the binders may be applied to fibers before, subsequent, or simultaneously with addition of the particles. Simultaneous addition can be accomplished by two separate streams of particles and binder that are simultaneously directed at a fibrous substrate, or alternatively merged immediately prior to impacting against the substrate.

Binding is performed under conditions that favor formation of hydrogen bonds or coordinate covalent bonds, and discourage formation of covalent bonds. Conditions that favor covalent bonds are those disclosed in U.S. Pat. No. 4,412,036 and U.S. Pat. No. 4,467,012 wherein particle and binder would be laminated between tissue layers under high temperature and pressure to form laminated adherent tissue layers. That patent teaches that minimal adhesion occurs at 200 pli (pounds per linear inch, as in a calendar press) if no external heat is supplied, but adhesion improves as the reaction temperature increases. Improved adhesion of the tissue layers occurs because of enhanced covalent bonding as the temperature increases.

Conditions that favor covalent bond formation are also shown in European Patent Applications 440 472 A1; 427 317 A2; 427 316 A2; and 429 112 A2. These European publications use polycarboxylic acid crosslinkers, and require elevated temperatures (for example above 145° C.) and acidic conditions (pH less than 7) to promote formation of intrafiber covalent ester bonds and inhibit reversion of the ester bonds. The present invention, in contrast, can form hydrogen or coordinate covalent bonds below 145° C., below 100° C., and even at room temperature. The binders of the present invention can also bind particles to fibers under neutral or alkaline conditions, i.e., at a pH above 7, but preferably at a pH of 5–8 or 7–8.

The intrafiber covalent bond forming processes described in the above European publications require formation of an anhydride that then reacts with a hydroxy group on cellulose to form a covalent ester bond. The presence of more than about 20% water by weight in the fibers interferes with formation of the anhydride and inhibits covalent bond formation. Hence, in processes that use binders that are also crosslinkers (polycarboxylic acid, polyols and polyamines) as binders in the present invention, the fibers should contain at least 20% water by weight (more preferably 30%) if the particles and binder are present in the fibers when curing occurs. The water inhibits covalent bond formation, and prevents all of the binder from being used to form covalent intrafiber crosslinks. Hence, some of the binder remains available to form the non-covalent bonds with the particles and produce ease of densification in fiber products made by the process of the present invention.

The present invention, in contrast, produces a product under conditions that favor formation of hydrogen or coordinate covalent bonds. Hence, the particles can be bound to the fibers in the absence of the external application of heat or pressure. Particles may also be bound and the resulting fiber product densified, for example at less than 200 pli (about 8000 psi), or less than 100 pli (about 4000 psi), in the absence of external application of heat to produce a product in which a substantial portion of the particles are bound by non-covalent bonds (hydrogen or coordinate covalent bonds). A substantial portion of particles bound by non-covalent bonds means at least half of the particles are bound by other than covalent bonds, for example by hydrogen or coordinate covalent bonds.

In yet other examples, particles may be bound in the absence of external application of pressure, but at elevated temperatures.

In particularly preferred embodiments, the particles are substantially entirely bound to the fibers. non-covalently.

Binding Examples for Polymeric Binders

Several examples are given below illustrating use of the polymeric binders of the present invention to attach superabsorbent particles to southern bleached kraft pulp.

EXAMPLE I

A 321 gram amount of NB-416 southern bleached kraft fluff obtained from Weyerhaeuser Company may be air-entrained in a blender-like mixing device and 100 grams of poly(caprolactone) diol (average molecular weight 2000, supplied by Aldrich Chemical Company of Milwaukee, Wis.) dissolved in 100 ml of deionized water may be sprayed onto the fluff as a binder. Then 435 grams of starch graft polyacrylate hydrogel fines (IM 1000F; supplied by Hoechst-Celanese of Portsmouth, Va.) may be added and mixed. The product may then be removed from the blender, and spread out in a fume hood to air dry overnight. The resulting product may then be airlaid on a small airlay line, from M & J Machines (of Horsens, Denmark) and thermobonded at 140° C. for one minute to produce a web containing 40% superabsorbent particles (SAP) attached to the individualized fibers. This binder has a low melting point, hence raising the temperature to 140° C. melts the binder and allows it to flow over the fibers and particles to enhance hydrogen bonding interactions and provide mechanical encapsulation that further binds the fibers and particles. This is an example of activating a solid binder by heating it, without liquid addition. A polypropylene glycol/polyethylene glycol copolymer binder would also behave in this manner.

EXAMPLE II

A 321 gram amount of southern kraft fluff was air-entrained in a blender-like mixing device and 154 grams of a 65% solution of polyacrylic acid (average molecular weight=2,000; supplied by Aldrich Chemical Company of Milwaukee, Wis.) diluted with 100 ml of deionized water was sprayed onto the fluff. Then 435 grams of polyacrylate hydrogel (FAVOR 800 supplied by Stockhausen of Greensboro, N.C.) was added into the mixing device and mixed with the fluff and polyacrylic acid binder. The product was removed and spread out to dry and then fed to a hammermill with a three-eighths inch round hole screen and shunted to a small airlay line to produce a web containing 40% SAP attached to the individualized fibers.

EXAMPLE III

A 321 gram amount of southern bleached kraft fluff is air-entrained in a blender-like mixing device and 100 grams of polyglycine (molecular weight=5,000–15,000; supplied as a dry powder by Sigma Chemical Company of St. Louis, Mo.) diluted with 100 ml of deionized water is sprayed onto the fluff. Then 435 grams of starch graft polyacrylate hydrogel fines (IM 1000F; supplied by Hoechst-Celanese of Portsmouth, Va.) is added and mixed. The product is removed and spread out in a fume hood to dry overnight. The resulting product is fed into a Fitz hammermill with a three-eighths inch round hole screen and shunted to a small M & J airlay line to produce a web containing 40% SAP attached to the fibers.

EXAMPLE IV

A 321 gram amount of southern bleached kraft fluff is air-entrained in a blender-like mixing device and 200 grams of a 50% solution of polyethyleneimine (molecular weight=

50,000–100,000; supplied by ICN Biomedicals, Inc. of Costa Mesa, Calif.), or polyvinyl pyridine is sprayed on the fluff. Then 435 grams of starch graft polyacrylate hydrogel fines (IM 1000F; supplied by Hoechst-Celanese of Portsmouth, Va.) is added and mixed. The product is removed and spread out in a fume hood to dry overnight. The resulting product is fed into a Fitz hammermill with a three-eighths inch round hole screen and shunted to a small M & J airlay line to produce a web containing 40% SAP attached to the fibers.

The classes of polymeric binders that encompass those described in Examples I–IV are especially preferred over other multiple hydrogen bonding functionality polymers for a number of reasons. One important reason is that their functionalities produce very strong, effective hydrogen bonding. Other important reasons include their relative lack of reactivity (as compared with polyaldehydes or polyisocyanates) and their low toxicity (again, as compared with polyaldehydes or polyisocyanates).

EXAMPLE V

As previously described, repetition of a hydrogen bonding group on each repeating unit of a polymer has been found to produce a binder that provides superior binding of particles to fibers, as compared to polymeric binders in which the hydrogen bonding functionality is not present on all the repeating units. This example shows the difference in binding efficiency between a 20% carboxylated polymer and a 100% carboxylated polymer. A bound sample was prepared as in Example I using a 20% carboxylated ethylene acrylic acid copolymer and a 100% carboxylated PAA. A sample of each was subjected to the same mechanical agitation (to simulate machine processing required to make a web), screened through a descending series of sieves to remove unattached SAP, and subjected to an absorbent capacity test (less attached SAP would result in a lower absorbent capacity). The result of the test was measured by weighing the unabsorbed liquid (0.9% saline) from a standardized insult, hence a lower number indicates more liquid absorbed or higher absorbent capacity.

A sample of the 20% carboxylated polymer (15% of the total mix) gave a beaker test result of 19.5 grams. A similar sample of polypropylene glycol would give a result of about 20.0 grams. However, the hydrogen bonding functionality of PPG is not as efficient as the carboxyl functionality of PAA. A similar sample of polyacrylic acid (100% carboxyl functionality of PAA) gave a result of 11.3 grams. A comparison of the 20% and 100% carboxylated polymers shows a substantial increase in SAP binding efficiency, as measured by an increase in absorbency of the product.

Non-Polymeric Binding Examples

Several examples are given below illustrating use of several non-polymeric organic binders of the present invention to attach superabsorbent particles to southern bleached kraft pulp.

EXAMPLE VI

A 3171 gram amount of southern bleached kraft fluff was air-entrained in a blender-like mixing device and 1000 grams of glycerin (96%, USP; supplied by Dow Chemical Co. of Midland, Mich.) diluted with 300 ml of deionized water was sprayed onto the fluff. Then 4348 grams of starch graft polyacrylate hydrogel fines (IM 1000F; supplied by Hoechst-Celanese of Portsmouth, Va.) was added to the mixing device and mixed with the fluff and binder. The material was then shunted into a flash tube dryer at 142° F., blown into a cyclone and fed into a Danweb airlay machine to form a web containing bound 40% IM 1000F that is substantially immobile in the web because the particles are bound to the fibers instead of mechanically entrapped by the matrix.

EXAMPLE VII

A 900 gram amount of southern bleached kraft fluff pulp sheet was sprayed with a 50% solution of glycine (supplied as a dry powder by Aldrich of Milwaukee, Wis.) so that the moisture content was 17–21% as the sheet was fed into a Fitz hammermill fitted with a three eighths inch hole screen. Starch graft polyacrylate hydrogel fines (IM 1000F; supplied by Hoechst-Celanese of Portsmouth, Va.) were simultaneously added to the mill by a screw feed device, mixed with the fluff, shunted to an M & J airlay forming machine and airlaid to form a web. The web that resulted contained 20% SAP attached to the fibers substantially uniformly throughout the web without being confined to a surface of the web.

EXAMPLE VIII

A 900 gram amount of southern bleached kraft fluff pulp sheet was sprayed with a 50% solution of pentaerythritol (supplied by Aldrich of Milwaukee, Wis.) so that the moisture content was 17–21% as the sheet was fed into a Fitz hammermill fitted with a three eighths inch hole screen. Starch graft polyacrylate hydrogel fines (IM 1000F; supplied by Hoechst-Celanese of Portsmouth, Va.) were simultaneously added to the mill by a screw feed device, mixed with the fluff, shunted to an M & J airlay forming machine and airlaid to form a web. The web that resulted contained 20% SAP attached to the fibers.

EXAMPLE IX

A 900 gram amount of southern bleached kraft fluff pulp sheet was fed into a Fitz hammermill fitted with a three eighths inch hole screen. The sheet was defiberized, shunted to an M & J airlay line, and airlaid into a web. As the web emerged, target zones of the web were misted with a 50% solution of lactose to raise the moisture content to 17–21%. Five gram aliquots of starch graft polyacrylate hydrogel fines (IM 1000F; supplied by Hoechst-Celanese of Portsmouth, Va.) were subsequently sifted onto the target zones. The web that resulted contained target zones with 5 grams of SAP attached to the fibers of each target zone. Portions of the web that were not targeted for lactose application did not adhere the particles well. This is an example of applying the binder to a target zone so that SAP primarily adheres to the target areas where the binder was applied. Target zone application of SAP can be advantageous because it reduces the cost of the product to provide SAP only in areas of a product where the SAP is needed, for example, the crotch area of a diaper. Placement of SAP in the area where a liquid insult is expected also decreases the necessity for wicking liquid to a SAP impregnated region. This is an advantage because the requirement for wicking can increase liquid leakage in an absorbent product such as a diaper.

EXAMPLE X

A 321 gram amount of southern bleached kraft fluff was air-entrained in a blender-like mixing device and 100 grams of glycerin (96%, USP; supplied by Dow of Midland, Mich.) diluted with 30 ml of deionized water was sprayed onto the fluff. 71 grams of Abscents (an odor absorbing zeolite supplied by UOP of Tarrytown, N.Y.) was then added and mixed in the mixing device with the fibers and glycerin for 15 seconds until a homogenous mixture was achieved. The material was then spread out in a fume hood overnight to dry, airlaid into a web and tested for particulate retention by an ash test. The pad so produced contained 7% particulate. The original addition amount should have produced 15%, hence 50% particle retention was observed. This compares favorably to particulate retention with latex binders under similar conditions in which only about 3% of particles are retained.

Product Characteristics

The following examples illustrate how SAP retention, pad integrity, wettability, bulk and liquid retention are affected by the glycerin binder of the present invention.

EXAMPLE XI

Superabsorbent particles were bound to cellulose fibers with a glycerin binder, as described in Example I above. For purposes of comparison, superabsorbent particles were bound to a separate sample of cellulose fibers using a polyvinyl acetate (PVAc) binder that was about 3% carboxylated, that is only about 3% of the PVA monomers were carboxylated. Binding was performed as in Example I, but PVAc was substituted for glycerin. A 100 gram sample of the glycerin and PVAc treated fluff with attached SAP was fed into a fan that was connected by a hose to a small cyclone mounted on top of a material containment box. This was done in an effort to simulate forces of mechanical agitation the fluff would encounter during the airlay process. After collection in the material containment device, fiber with attached SAP was removed and weighed. A five gram sample of the fiber with attached SAP was then placed in a column of sieves with decreasing mesh sizes and subjected to a shaking and thumping action for ten minutes in order to further dislodge any poorly attached SAP. Unattached or poorly attached SAP sifted through screens having a range of 5–60 mesh, while the fiber with well attached SAP remained on the 5 mesh screen.

A 2.00 gram sample of the fibers that remained near the top of the sieve column was then placed in a 75 ml sample of 0.9% saline for exactly one minute. After that minute, the liquid that was not absorbed was poured off into a separate, tared beaker and weighed. The relative amounts of liquid absorbed is indicative of the amounts of SAP bound to the fiber. Fiber retaining higher amounts of SAP tend to absorb more water and give a smaller amount of liquid not absorbed.

These results are shown in Table I:

TABLE I

| Glycerin Binder Comparing SAP Retention with Glycerin and PVAc Binders | |
|---|---|
| Binder | Beaker result |
| 40-504 (PVAc) | 22.8 g |
| 3666H (PVAc) | 22.0 g |
| Glycerin | 5.5 g |

Table I illustrates that the glycerin binder provides a product that has an absorbency increase of 400% compared to the PVAc binder. A substantial portion of this improvement is believed to be due to better adhesion between the fibers and SAP, such that the particles are not dislodged from the fibers.

EXAMPLE XII

Pad integrity was compared in fibrous products that used no binder and a glycerin binder at 7% and 11% by weight. Each of these binders was used to bind SAP to fibers as in Example I, and properties of the pad were measured and are shown in Table II:

TABLE II

| | Tensile Results | | |
|---|---|---|---|
| Sample | Basis Weight | Density | Tensile Index |
| Pad integrity (low density): | | | |
| NB-416 (control) | 464 gsm | 0.12 g/cc | 0.257 Nm/g |
| NB-416/7% Glycerin | 437.6 gsm | 0.126 g/cc | 0.288 Nm/g |
| NB-416/11% Glycerin | 402.5 gsm | 0.135 g/cc | 0.538 Nm/g |
| Pad Integrity (high density): | | | |
| NB-416 (control) | 482.1 gsm | 0.218 g/cc | 0.475 Nm/g |
| NB-416/7% Glycerin | 460.7 gsm | 0.219 g/cc | 0.882 Nm/g |
| NB-416/11% Glycerin | 421.6 gsm | 0.248 g/cc | 1.536 Nm/g |

The glycerin binder in this example produced a product that had a higher tensile index than an untreated product. The increased tensile strength was especially enhanced in the densified product.

EXAMPLE XIII

The effect of binders on the wettability and bulk of fibers was tested using the following fibers: NB-316 (a standard southern bleached kraft pulp with no binder); GNB 25% (a standard southern bleached kraft pulp with 25% glycerin (entrained and sprayed); HBA (a high bulk intrafiber crosslinked fiber available from the Weyerhaeuser Company that contains intrafiber covalent crosslinks); and GHBA (HBA fibers treated with a glycerin binder) in amounts of 12.5% and 25% by weight. Results are given in Tables III and IV.

FAQ time was determined by airlaying a specific quantity (4.00 grams) of the fluff to be tested into a clear plastic tube that was fitted with a screen at one end. The fluff and tube were then placed into a well in the test device and a metal plunger was lowered onto the fluff and the pad's bulk calculated. Water then flowed from underneath the pad, passed through the screen and wicked up through the pad. Absorbency time was measured from when the liquid makes contact with the bottom screen until the water completes an electrical circuit by contacting the foot of the plunger resting on top of the pad. Lower absorbency times indicate better absorbency. Since the absorption of the liquid by the pad was accompanied with some collapse of the pad's structure, the bulk of the wet pad was then recalculated. The amount of liquid absorbed was then measured and a gram per gram capacity for the material was calculated.

Table III gives FAQ time as a measure of wettability. A lower FAQ time indicates a product that is more absorbent and wicks faster. Table IV gives wet bulk of fibers and the adjusted bulk of the fibers. The adjusted bulk is a calculated number obtained by dividing the bulk by the actual percent of pulp in the sample.

TABLE III

| Fiber | Wettability FAQ time |
| --- | --- |
| NB-316 | 3.0 sec |
| GNB 25% | 3.2 sec |
| HBA | 13.5 sec |
| GHBA 12.5% | 4.5 sec |
| GHBA 25% | 0.4 sec |

TABLE IV

| Fiber | Bulk Wet Bulk | Adjusted Bulk |
| --- | --- | --- |
| NB-316 | 12.7 cc/g | 12.7 cc/g |
| GNB 25% | 10.9 cc/g | 14.5 cc/g |
| HBA | 19.4 cc/g | 19.4 cc/g |
| GHBA 12.5% | 16.1 cc/g | 18.4 cc/g |
| GHBA 25% | 14.9 cc/g | 19.9 cc/g |

The low FAQ times (Table III) in the glycerin treated fibers (GNB, GHBA) show that wettability is as good as the untreated fiber (NB-316). The GHBA 25% had significantly better wettability than untreated HBA. Bulk of glycerin treated fibers (Table IV) was not significantly decreased or changed at all levels of glycerin binder on a fiber to fiber comparison basis.

EXAMPLE XIV

Liquid retention of bound fibers was determined and compared to fibers in which no binder was added. NB-316 is a pulp sheet available from Weyerhaeuser Company in which no binder is used. HBA is described in Example X. HBA/Gly SAP was an HBA fiber that was bound with glycerin (12% binder, 48% fiber) and which contained 40% SAP particles. NB-316/Gly SAP is NB-316 fibers to which glycerin and SAP fibers were added.

The procedure for determining liquid retention was to weigh triplicate small portions (near 0.2 grams) of samples to the nearest 0.0001 gram and then heat seal the small portions inside an envelope of a heat sealable nonwoven tea bag. The samples were then immersed in an excess of 0.9% saline for thirty minutes, then drained by suspending them from a clip for fifteen minutes. The samples were weighed to determine the amount of liquid absorbed. The grams of liquid absorbed per gram of sample was calculated and the samples were spun in a centrifuge for one minute. The samples were then reweighed and a percent liquid retention was calculated.

Results are shown in the following Table V:

TABLE V

| Liquid Retention (after centrifuge) | |
| --- | --- |
| Fiber/Binder | % Retention |
| NB-316/none | less than 1% |
| HBA/none | less than 1% |
| HBA/Gly SAP | 23% |

TABLE V-continued

| Liquid Retention (after centrifuge) | |
| --- | --- |
| Fiber/Binder | % Retention |
| NB-316/Gly SAP | 31.5% |

The results in Table V illustrate that fibers that have SAP bound to them retain liquid well, while fibers without SAP retain liquid poorly. The glycerin binders provided excellent adherence of SAP to the fibers.

EXAMPLE XV

Auxiliary Binder

As previously described, an auxiliary binder can be used in addition to the non-polymeric binders of the present invention. A 321 gram amount of a southern bleached kraft fiber (NB-416, supplied by Weyerhaeuser) was air entrained in a blenderlike mixing device and sprayed with 212.8 grams of a polyvinylacetate latex (PN-3666H, supplied by H B Fuller of Minneapolis, Minn.). While still mixing, 438 grams of a water swellable polyacrylate hydrogel (Favorsab 800, supplied by Stockhausen of Greensboro, N.C.) was added and the resulting mixture was then sprayed with 100 grams of a 50% solution of glycerin (supplied by Dow of Midland, Mich.). The blender was then stopped and the mixture was vacuumed from the blender and placed in a fume hood to air dry overnight. The dried product was then airlaid into a 6" diameter pad in a laboratory padformer, pressed to a density of approximately 0.077 g/cc, and thermobonded at 140° C. for thirty seconds. The resulting pads had 40% bound SAP and improved tensile strength as compared to untreated fluff with SAP and as also compared to binder treated fluff with SAP without the auxiliary binder.

Tensile strength was highest with polyvinylacetate alone, followed by a combination of polyvinylacetate and glycerin, then glycerin alone. Lowest tensile strength was seen with no binder at all.

EXAMPLE XVI

Binders of the present invention may be used to bind particles to pulp fibers that contain synthetic thermobonding fibers. In this example, KittyHawk pulp (available from Weyerhaeuser Company) is a mixture of NB316 southern bleached kraft and 22% polyethylene thermoplastic binder fibers. The KittyHawk pulp is used to produce a pulp web, with SAP bound to the fibers as described in Example III. The web with adhered SAP is then passed through a thermobonder to soften the polyethylene fibers and fuse the fibers of the web to each other to increase web strength.

EXAMPLE XVII

Solid sample $^{13}$C NMR spectra were obtained on cellulose fibers treated with ascorbic acid to bind SAP to the fibers. An NMR spectra was also obtained on L-ascorbic acid. In both cases, separate spectra were acquired using recovery delays of 1 sec and 5 sec between acquisitions.

The peaks in the treated fiber spectrum were assigned readily to the components: SAP polyacrylate carboxyl (185 ppm) and backbone (50–30 ppm) carbons; cellulose (106, 90, 84, 76, 73 and 66 ppm); and ascorbic acid ring carbons C-1, C-2 and C-3 (175, 119 and 156/153 ppm, respectively); the other ascorbic acid carbons are in the cellulose region, two of them being resolved at 69 and 61 ppm. The ascorbic acid carbon chemical shifts in this ternary mixture were essentially identical (±0.2 ppm) to their values in pure ascorbic acid. This indicated that the ascorbic acid in the treated fibers had undergone no gross structural changes, such as total neutralization, oxidation or ring opening.

The signal-accumulation rates observed at the two different recovery delay times showed that the proton spins in pure ascorbic acid relaxed after excitation much more slowly than they did in the ternary mixture. As shown in the following table, slow relaxation yields higher signal strength at the long recovery delay relative to the short one. The fast proton spin-lattice relaxation in the coated fibers indicated that the ascorbic acid in this system is held more tightly in place (i.e., is less mobile) than in the bulk acid. The ascorbic acid is apparently held tightly by one or both of the other two components, cellulose and SAP, and not by other ascorbic acid molecules.

If the bonding were purely ionic, involving ascorbate ion and an acrylic acid unit in the SAP, then the NMR of the treated fibers would show the ascorbic acid in the salt form. NMR reference spectra were found of the acid and its salt in aqueous solution, and C-3 is seen to shift dramatically on ionization of its OH group: 156 ppm in the acid to 176 ppm in the salt. Thus, since the NMR spectrum of the ternary mixture contains the peaks at around 156 ppm, the ascorbic acid in this system is not ionized.

The infrared spectra, however, point to substantial disruption in the structure of the ring OH groups, comparing pure ascorbic acid with the treated fibers, with the ascorbic acid in the mixture resembling ascorbate salts in having some of the OH stretching bands missing.

Looking at acidities, ascorbic and polyacrylic acids have nearly identical $pK_a$, values (4.2 vs 5, respectively). They are both typical strong organic acids with weak conjugate bases. Thus, there is no compelling reason for one of these acids to be neutralized (ionized) by the conjugate base of the other acid. Rather, there should be a strong tendency for an ascorbic acid and an acrylate ion to share a hydrogen ion between them, resulting in a long hydrogen bond between partially ionic ascorbic and acrylic acid units. This sharing of hydrogen ions would certainly be reflected in the IR spectrum, yet satisfies the NMR data by not invoking full ionization of ascorbic acid. The spectroscopic data are fully consistent with a hydrogen bonding mechanism between ascorbic acid and an acrylate unit in the superabsorber.

| Acrylic Acid NMR Amplitude Ratios at Different Recovery Delay Times. | | |
|---|---|---|
| | Signal Ratio, 5 sec/1 sec | |
| Peak Freq., ppm | Treated Fibers | Pure Acid |
| 176 | 1.99 | 5.21 |
| 156 | 1.92 | — |
| 153 | 1.80 | 5.35 |
| 119 | 2.10 | 4.26 |

EXAMPLE XVIII

Fibers With Superabsorber And Ascorbic Acid

Infrared Analysis

Infrared transmission spectra of the untreated NB316 pulp, the treated NB316 pulp, ascorbic acid, and the IM 100F superabsorber were prepared. Then, a subtraction spectrum representing the treated pulp minus the untreated control was obtained.

Examination of that subtraction spectrum indicated several infrared bands that were obviously associated with the ascorbic acid. They were evident at 1755, ~1690 (shifted slightly from 1660–1670), 868, 821, and 756 wavenumbers ($cm^{-1}$). However, several other bands that were prominent in the ascorbic acid spectrum were absent in that subtraction spectrum. They included the following: 3525, 3410, 3318, 1319, 1119, and 1026 $cm^{-1}$.

The higher frequency bands (3300–3600 $cm^{-1}$) in ascorbic acid are indicative of bonded OH groups. The infrared bands at 1319, 1119, and 1026 $cm^{-1}$ may also be associated with OH vibrations. Consequently, the IR suggested that the subtraction spectrum reflected primarily a loss of the OH groups that were attached directly to the ring. A likely possibility is that the OH groups were replaced by sodium. The only other major band in the subtraction spectrum was located at 1589 $cm^{-1}$. This was probably due to the superabsorber C=O which had shifted to a slightly higher frequency (from 1562 $cm^{-1}$).

EXAMPLE XIX

Activation

The binders of the present invention have the advantage of being activatable by addition of liquid or by heating. "Activation" includes activating a previously inactive binder (e.g., by adding liquid to a solid) or reactivating a previously active binder (e.g., by adding liquid to a dried liquid binder) on the fibers. Hence, a liquid binder can be applied to cellulose fibers, loose or in another form, such as a cellulose mat, in the absence of the particles to be bound. The binder is then dried or allowed to dry, for example until the binder and fiber reach an equilibrium moisture content with ambient air. Alternatively, the binder can be applied as a solid, for example, particles sprinkled onto a fiber mat. At a later stage of processing, a liquid such as water is added to the fibers resulting in an activation of the binder. The particulates may then be added, and the binder secures the particulates to the fibers. This subsequent processing of the fibers to attach the particles can occur, for example, at a separate location from the location where the binder was applied to the fibers. Therefore, manufacturers of products can add particulates of interest (e.g., superabsorbent particles or fibers; antimicrobial particles, etc.) at the place of manufacture of the end products that incorporate the treated fibers. Also, more than one type of particulate material may be added, if desired.

It has also been found that some of the binders of the present invention can be reactivated by mechanical agitation. For example, glycerin binder may be applied to fibrous cellulose. The glycerin binder may be allowed to dry overnight, and the fibers then mechanically agitated in the presence of superabsorbent particles to reactivate the glycerin binder and bind the particles to the fibers. Mechanical agitation may take place, for example, in a defiberizer where a sheet or mat of glycerin treated cellulose fibers are defiberized while being intimately mixed with SAP that is bound to the fibers by the mechanical agitation.

Binder Activation Examples

Binder reactivation in the present invention allows binder to be added to fibers either before or after particles are added to the fibers. The binder is subsequently activated by addition of liquid, heat, or agitation, and particles are bound to the fibers. The particles may be added to the fibers either before binder activation, after binder activation, or simultaneous with activation. If SAP is to be added to cellulose fibers, for example, the binder may be applied to a pulp sheet which is subsequently fiberized. A liquid such as water may be added to the pulp before or after fiberization, and SAP may be added before or after water addition, or simultaneously with the water. If SAP is added after water addition, the SAP should be applied to the fibers prior to complete evaporation of the added water from the fibers.

Activation can be of all the fibers, or only portions of the fibers, such as target zones or portions of the mat where particulate binding is desired. The particles may then be added to the mat and adhered to the target zones of the mat which have been activated. In some embodiments, the binder is applied as a solid and heated during a later processing stage to activate the binder by softening it such that it binds the particles to the fibers. The particles may be added in a pattern corresponding to a desired distribution of particles in the fibrous material. Most commonly, however, activation is accomplished by moistening a targeted area of the product into which an inactive (dry or dried) binder has already been introduced.

In yet other embodiments, the binder is applied to the fibers and then activated by applying kinetic energy to the fibers. Neat polypropylene glycol (MW 2000) binder, for example, may be sprayed on fibers and allowed to air dry. Desired particles are then added to the fibers as the fibers are mechanically agitated in a blender or defiberizer to kinetically activate the binder and bind the particles to the fibers. For kinetic activation, the binder may be added as a liquid or a solid to the fibers. In the case of liquid addition, the liquid is allowed to air dry, and then reactivated by mechanically agitating the fibers and binder. In the case of solid binder addition, the binder is applied as a solid, and then moistened (for example, to a total fiber moisture content of about 7%) and then mechanically agitated.

Activation of the binder may be performed prior to adding the particles, subsequent to adding the partices, or simultaneously with addition of the particles. Once the binder is activated, it adheres a substantial portion of the particles to the fibers, wherein "a substantial portion" refers to about half of the particles present in the fibers, at least where the particles are not added in excess.

In embodiments in which the binder is applied to the fibers as a solid, the activating step can comprise applying a liquid to the fibers after the binder has been applied to the fibers, shortly before the binder is applied to the fibers, or simultaneously with application of the binder to the fibers.

The activating step is preferably performed after the curing step is complete, if a curing step is to be performed.

The following example will illustrate several specific applications of the activation process, and are not intended to limit the invention to the disclosed methods.

EXAMPLE XX

The method of Example I above could be modified such that the SAP is not added until after the web is heated to 140° C. A solid polyethylene glycol/polypropylene glycol copolymer could be substituted for the binder of Example I, and it would melt well below 140° C., and in its liquid form bind the SAP to the fibers. The SAP could be applied randomly across the heated product, or applied specifically to a targeted zone of the product where enhanced absorbency is specifically desired.

EXAMPLE XXI

A southern kraft pulp sheet would be immersed or sprayed with 154 grams of a 65% solution of polyacrylic acid diluted with 100 ml of deionized water. The sheet is then allowed to air dry overnight, heated in an oven at 80° C. for thirty minutes and conditioned in a 50% relative humidity chamber overnight. The sheet is then misted with water to raise its moisture content to 17–20% as it is fed into a Fitz hammermill filled with a three-eighths inch hole screen. Polyacrylate hydrogel particles of FAVOR 800 supplied by Stockhausen would simultaneously be added to the mill by a screw feed device, mixed with the fluff, shunted to an M & J airlay forming machine and airlaid to form a web containing bound SAP throughout the web, i.e., without being confined to a surface of the web. Mixing SAP throughout the fluff helps produce a product in which SAP is homogeneously or randomly distributed, which diminishes problems of gel blocking.

EXAMPLE XXII 900 grams of KittyHawk pulp sheet (from the Weyerhaeuser Co., containing 22% synthetic fiber) is immersed in a 10% by weight solution of polyglycine for thirty minutes. The 5 inch wide sheet was then uncoiled on a lab bench to air dry overnight, heated in an oven at 80° C. for thirty minutes and conditioned in a 50% relative humidity chamber overnight. The sheet is fed into a Fitz hammermill fitted with a three-eighths inch hold screen, defiberized, shunted to an M & J airlay line, and airlaid into a web. As the web emerges, circular target zones of the web are misted with water from a spray bottle to raise the moisture content to 17–21% in the target zone. Five gram aliquots of starch graft polyacrylate hydrogel fines (IM 1000F; supplied by Hoechst-Celanese of Portsmouth, Va.) are subsequently sifted onto the target zones to yield a web with SAP bound in target zones. The SAP does not form a confluent layer, but is instead present in particulate form on and below the surface of the web.

EXAMPLE XXIII

A 900 gram amount of southern bleached kraft fluff pulp sheet is sprayed with a 50% solution of polyglycine so that the moisture content is 17–21% as the sheet is fed into a Fitz hammermill fitted with a three-eighths inch hole screen. Starch graft polyacrylate hydrogel fines (IM 10000F; supplied by Hoechst-Celanese of Portsmouth, Va.) are simultaneously added to the mill by a screw feed device as the sheet is fed into the hammermill, mixed with the fluff, shunted to an M & J airlay forming machine and airlaid to form a web. The fines are intimately mixed with the fluff in the fibermill and bound to the fibers by the polyglycine binder to produce a web with particles distributed throughout its width, and not restricted to a superficial surface.

EXAMPLE XXIV

A 900 gram amount of a southern bleached kraft pulp sheet was immersed in a 2% by mass solution of ascorbic acid (supplied as a dry powder by Aldrich Chemical Co. of Milwaukee, Wis.) for thirty minutes. The 5 inch wide sheet was then uncoiled on a lab bench to air dry overnight, heated in an oven at 80° C. for thirty minutes and conditioned in a 50% relative humidity chamber overnight. The sheet was then gravimetrically determined to be about 7% by weight ascorbic acid. The sheet was misted with water to raise its moisture content to 17–20% as it was fed into a Fitz hammermill fitted with a three eighths inch hole screen. Misting with water reactivated the binder prior to addition of superabsorbent particles (SAP). Starch graft polyacrylate hydrogel fines (IM 1000F supplied by Hoechst-Celanese of Portsmouth, Va.) were added as SAP to the hammermill by a screw feed device, mixed with the fluff, shunted to an M & J airlay forming machine (from Horsens, Denmark) and airlaid to form a web. The web that resulted contained 20% SAP attached to the fibers by the binder.

EXAMPLE XXV

A 900 gram amount of KittyHawk pulp sheet (from the Weyerhaeuser Co., containing 22% synthetic fibers) was immersed in a 10% by weight solution of urea (supplied by Aldrich of Milwaukee, Wis.) for thirty minutes. The 5 inch wide sheet was then uncoiled on a lab bench to air dry overnight, heated in an oven at 80° C. for thirty minutes and conditioned in a 50% relative humidity chamber overnight. The sheet was then gravimetrically determined to be about 30% by weight urea. The sheet was fed into a Fitz hammermill fitted with a three eighths inch hole screen, defiberized, shunted to an M & J airlay line, and airlaid into a web. As the web emerged, the binder in the dried web was reactivated by misting target zones of the web with deionized water in a circular pattern from a spray bottle to raise the moisture content of the web or the target zones to 17–21%. Five gram aliquots polyacrylate hydrogel (FAVOR 800 supplied by Stockhausen of Greensboro, N.C.) were subsequently sifted onto each reactivated target zone. The web that resulted contained target zones with 5 grams of SAP attached to the fibers in each target zone. Alternative spray patterns could be provided by selecting spray heads or different control devices that mist different patterns.

Thermoplastic Binders

An auxiliary binder may also be used to help bind fibers to each other above the melting point of the auxiliary binder. The auxiliary binder may be a solid thermoplastic material that is applied to the fibers and softened by elevating the temperature during the binding step to above the softening temperature of the auxiliary binder. The auxiliary binder is thereby temporarily softened, rendered more fluid (which for purposes of convenience may be referred to as auxiliary binder melting) and subsequently resolidified as the temperature cools, which thermoplastically binds the fibers to each other, and the particles to the fibers. The auxiliary binder may also contain a hydrogen bonding functionality that hydrogen bonds the particles to the fiber. Examples of auxiliary binders that are thermoplastic and also contain hydrogen bonding groups include ethylene vinyl alcohol, polyvinyl acetate, acrylates, polycarbonates, polyesters and polyamides. Further information about the use of such auxiliary binders can be found in U.S. Pat. No. 5,057,166.

The auxiliary or second binder can be added to the fibers, either before or after a first binder, to help bind the fibers to each other and provide additional binding between the fibers and particles. A suitable second binder would be a thermoplastic or thermosetting binder. In the case of thermoplastic polymers, the polymers may be a material which remains permanently thermoplastic. Alternatively, such polymers may be a material which is partially or fully crosslinkable, with or without an external catalyst, into a thermosetting type polymer. As a few specific examples, suitable thermoplastic binders can be made of the following materials ethylene vinyl alcohol
polyvinyl acetate
acrylic
polyvinyl acetate acrylate
acrylates
polyvinyl dichloride
ethylene vinyl acetate
ethylene vinyl chloride
polyvinyl chloride
styrene
styrene acrylate
styrene/butadiene
styrene/acrylonitrile
butadiene/acrylonitrile
acrylonitrile/butadiene/styrene
ethylene acrylic acid
polyethylene
urethanes
polycarbonate
polyphenylene oxide
polypropylene
polyesters
polyimides In addition, a few specific examples of thermoset binders include those made of the following materials:

epoxy
phenolic
bismaleimide
polyimide
melamine/formaldehyde
polyester
urethanes
urea
urea/formaldehyde More than one of these materials may be used to treat the fibers. For example, a first coating or sheath of a thermoset material may be used followed by a second coating of a thermoplastic material. The superabsorbent particles or other particles are then typically adhered to the outer binder material. During subsequent use of the fibers to make products, the thermoplastic material may be heated to its softening or tack temperature without raising the thermoset material to its curing temperature. The remaining thermoset material permits subsequent heating of the fibers to cure the thermoset material during further processing. Alternatively, the thermoset material may be cured at the same time the thermoplastic material is heated by heating the fibers to the curing temperature of the thermoset with the thermoplastic material also being heated to its tack temperature.

certain types of binders enhance the fire resistance of the treated fibers, and thereby products made from these fibers. For example, polyvinyl chloride, polyvinyl dichloride, ethylene vinyl chloride and phenolic are fire retardant.

Surfactants may also be included in the liquid binder as desired. Other materials may also be mixed with the liquid binder to impart desired characteristics to the treated fibers. For example, particulate material, such as pigments, may also be included in the binder for application to the fibers.

EXAMPLE XXVI

As previously described, an auxiliary binder can be used in addition to the polymeric binders of the present invention.

A 3210 gram amount of southern bleached kraft binder (NB-416, supplied by Weyerhaeuser Company) is air entrained in a blenderlike mixing device and sprayed with 2128 grams of a polyvinyl acetate latex (PN-3666H, supplied by H. B. Fuller of Minneapolis, Minn.). While still mixing, 4073 grams of a water swellable polyacrylate hydrogel (IM 1000-60, supplied by Hoechst-Celanese of Portsmouth, Va.) is added and the resulting mixture is then sprayed with 1160 grams of a 50% solution of polypropylene glycol (supplied by Union Carbide of Danbury, Conn.). The blender is then stopped and the mixture was shunted into a flash tube dryer. The dried product is then airlaid as a 16 inch wide web on a Danweb airlay machine, pressed to a density of approximately 0.15 g/cc, and thermobonded at 140° C. for thirty seconds. The resulting web would have 40% bound SAP and improved tensile strength (as compared to untreated fluff with SAP).

Application of Binder

The binders of the present invention can be added to the fibers in any convenient manner. One such procedure is to spray the binder or binders on a web of the fibers that is conveyed past a sprayer on a conveyor belt. ,Alternatively, loose fibers may be allowed to fall past a sprayer, or loose fibers may be moved on a conveyor belt past a sprayer. The loose fibers may also be slurried with or immersed in binder. For solid binders, blending of the fiber and binder may be accomplished or the binder may simply be sprinkled onto or otherwise comingled with the fibers. The fibers may also be sprayed or immersed in the binder, or binder particles may be applied thereto. These fibers can, while still wet in the case of a liquid binder or following reactivation of a liquid or solid, be combined with the particles. The fibers can also be allowed to dry for later reactivation with a reactivation liquid and combined with the particles at that time. Particles may be added from conventional volumetric feeders in a hammermill or from injectors on a paper making line.

One method for uniformly coating the fibers with a binder and adding the particles is shown in U.S. Pat. No. 5,064,689, which is incorporated herein by reference. However, the invention is not limited to any specific mechanism for combining the fiber, binder and particles.

Composite Absorbent Product

In accordance with the present invention, absorbent structures may be made from the fibers, with the bound particulates, in accordance with the present invention. These articles may be composite structures (e.g., made of plural materials). For example, the articles may have a core of plural types of fibers, or fiber layers, with or without covering materials. These products are capable of absorbing significant quantities of water and other fluids, such as urine and body fluids. Such products include, but are not limited to, disposable diapers, sanitary napkins, incontinent pads, towels and the like.

Figure 2:
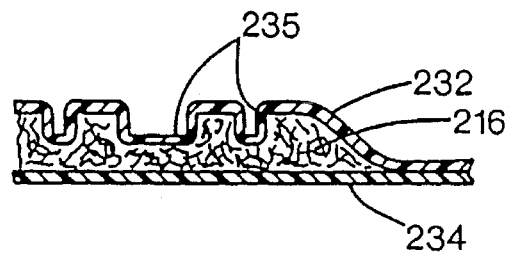
FIG. 2 represents a partial sectional view of the pad of FIG. 1.

As best shown in FIGS. 1 and 2, an absorbent towel 200 may have a core 216 with a cover sheet 232 and a backing sheet 234. The core 216 may be comprised of fibers with the binders of the present invention and particulate materials, such as superabsorbent particles secured to the fibers by the binder. The fibers that contain the binder may be blended with other fibers as well in the core. Cover sheet 232 is made of any suitable material, including liquid permeable, nonwoven materials, which will readily permit the passage of liquid through the cover sheet to the absorbent pad 216. The following list of liquid permeable materials is provided by way of example only: nonwoven sheets of polypropylene, rayon, nylon fibers, polyester fibers, and blends thereof. A specifically preferred cover sheet material for wipes is a 70% rayon/30% polyester blend having a basis weight of 21.5 grams/m$^2$, available from the Scott Paper Company.

The backing sheet 234 may be, but is not necessarily, made of a liquid impermeable material, including but not limited to, films of polyethylene, polypropylene and polyester and blends thereof along with nylon and polyvinyl chloride films. A specifically preferred backing sheet material is a polyethylene film from Dow Chemical Company.

FIGS. 1–2 illustrate an absorbent pad structure which may be formed from fibers of the present invention, whether or not they are blended with other fibers. FIGS. 1 and 2 represent an absorbent pad having a heat embossed screen pattern. Pads having no pattern may also be used. A pad having a cover sheet and a backing sheet may be formed, for example, by placing a square fiber piece cut from the sheet onto a corresponding precut backing sheet. A corresponding precut cover sheet is placed over the top of the fiber on the backing sheet. This assembly may then be adhesively bonded.

Figure 3:
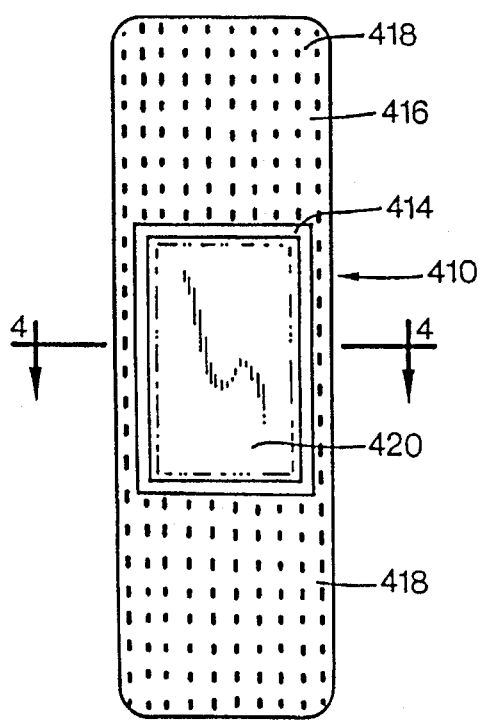
FIG. 3 illustrates a plan view of a bandage incorporating fibers of the present invention.
Figure 4:
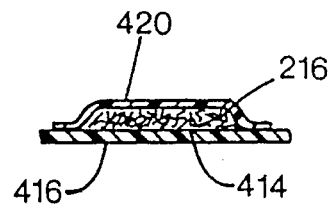
FIG. 4 is a sectional view of the bandage of FIG. 5, taken along line 4—4 of FIG. 3.

With reference to FIGS. 3–6, absorbent structures in the form of bandages or dressings are shown. In FIGS. 3 and 4, a bandage 410 for application to a wound to absorb blood and other bodily fluids is shown. An absorbent pad 216 (FIG. 4) is securely mounted to an exterior or pad mounting surface 414 of a backing strip 416. Any suitable mounting or securing means may be used to affix pad 216 to the surface 414 of the strip 416. However, it is preferable for surface 414 to be coated with an adhesive so that the pad 216 may be adhesively mounted in place. An exemplary adhesive is ethylene vinyl acetate adhesive. It is also desirable for the overall surface 418 of backing strip 416 to be coated with a conventional adhesive. Surface 418 is the surface which is affixed to the area of the skin surrounding the wound. Conventional "peel-back" tabs may be used to protect the adhesive coating and pad 216 until the bandage is to be applied. This type of backing strip is well known in the art.

The backing strip 416 may be of any known flexible material suitable for application to the skin. It is preferable for the strip 416 to be of a material which is impermeable to the passage of liquid so that fluid from a wound is contained by the bandage. However, the strip 416 may be apertured or otherwise breathable to permit air to reach the wound to promote the healing process. A specific example of a suitable backing strip 416 is a polyethylene film.

As in the other structures described, a variety of combinations of antimicrobials and other particles may be used in such a bandage. Again, however, the particles are adhered securely in place when the particles have a hydrogen bonding or a coordinate covalent bonding functionality, the fibers to which these particles are bound have a hydrogen bonding functionality, and wherein the binder is selected from the group consisting of a polypropylene glycol, a polypropylene glycol/polyethylene glycol copolymer, polyacrylic acid, a polyamide, or a polyamine and the polymeric binder has a hydrogen bonding or a coordinate covalent bond forming functionality on each repeating unit of the binder. Two different particles, such as antimicrobials in particulate form, may be adhered to the same fiber. In the alternative, each different type of antimicrobial particle or other particle may be adhered separately to different fibers. Also, blends of fibers may be included in absorbent structures such as pad 216. For example, these blends may include fibers with adhered antimicrobial (one or more antimicrobials) particles and adhered superabsorbent particles; fibers with one or more antimicrobial particles without superabsorbent particles blended with fibers having adhered superabsorbent particles with or without antimicrobial particles; and combinations of such fibers with untreated fibers and/or binder coated fibers without superabsorbent particles or antimicrobial particles. In addition, other particles, such as anticoagulants or hemostatics may be attached to the fibers.

The absorbent pad 216 of bandage 410 may also include a cover sheet 420. Cover sheet 420 is typically made of any suitable material which will readily permit the passage of liquid through the cover sheet to the absorbent pad 216, such as nonwoven fiber webs of fibers such as, for example, rayon, nylon, polyester, propylene and blends thereof. One specifically preferred cover sheet material is a 70 percent rayon/30 percent polyester blend having a basis weight of 18 g/m$^2$ from Scott Paper Company.

Figure 5:
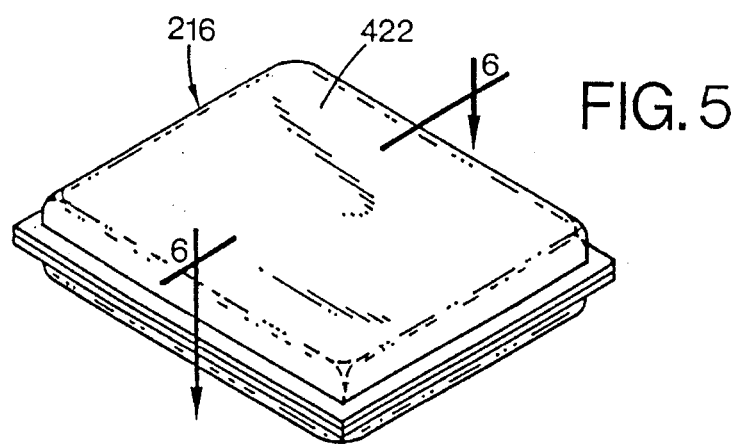
FIG. 5 is a perspective view of an absorbent structure of fibers of the present invention.
Figure 6:
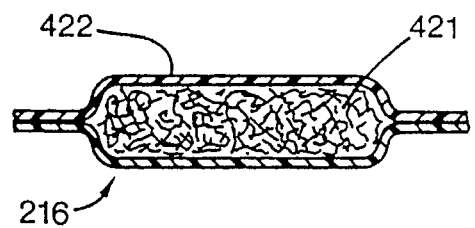
FIG. 6 is a cross-sectional view of the structure of FIG. 5, taken along line 6—6 of FIG. 5.

The dressing 216 shown in FIGS. 5 and 6 illustrates fibers 421 placed within an enclosure 422. Enclosure 422 has at least one liquid permeable surface through which fluid or liquid may pass to be absorbed by the fibers. The enclosure containing the loose fibers may be secured to the skin using adhesive tape, for example. Again, the fibers 421 preferably include antimicrobial particles attached to at least some of the fibers.

Figure 7:
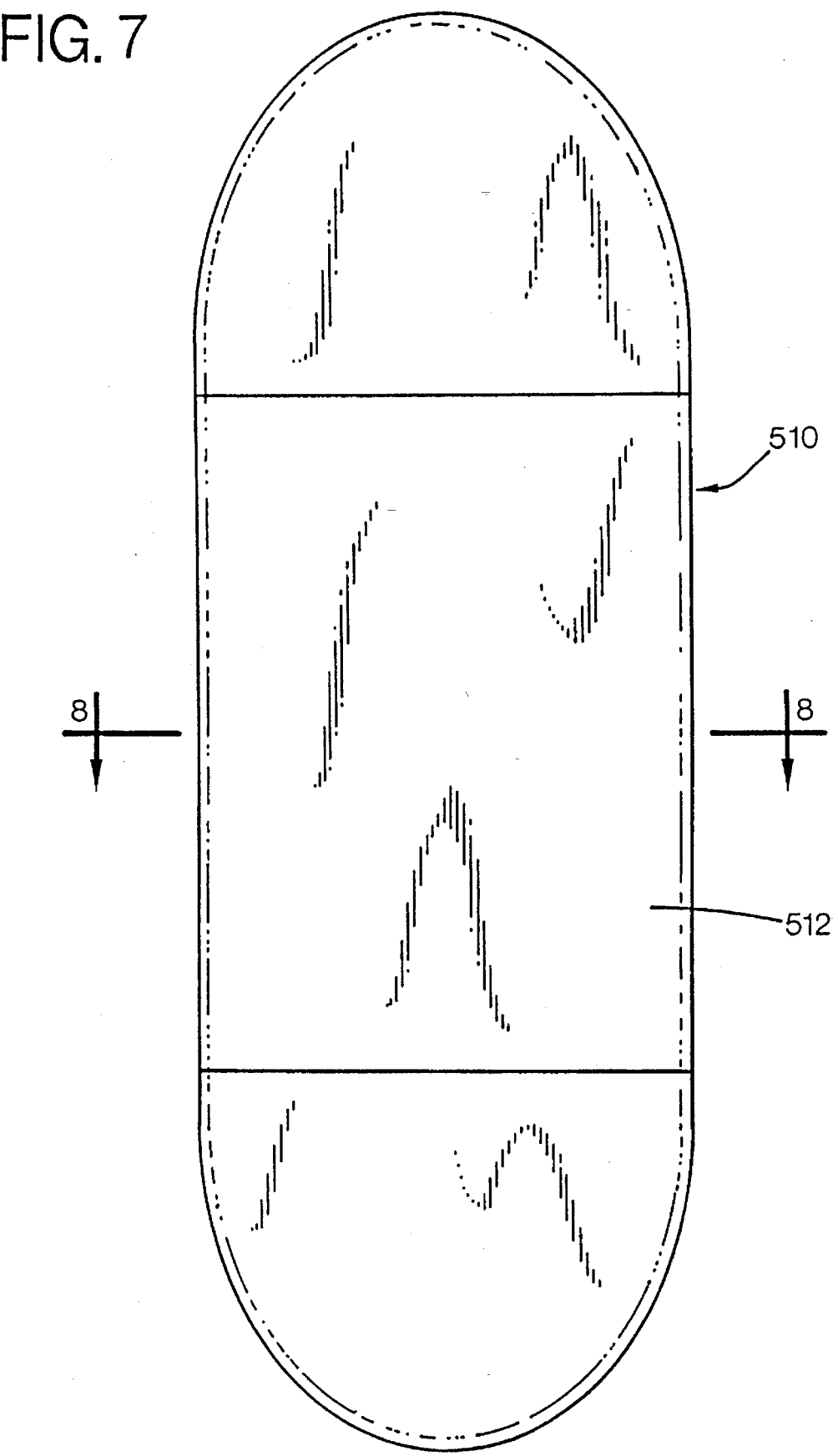
FIG. 7 is a plan view of a feminine hygiene appliance incorporating fibers of the present invention.

FIGS. 7 and 8 illustrate fibers of the present invention incorporated into a feminine hygiene appliance such as a feminine pad or tampon. In this case, the feminine pad 510 is illustrated as having a cover sheet 512. The loose fibers having adhered antimicrobial particles, which may alternatively be in the form of a pad, are included within the interior of the feminine appliance as indicated at 216 in FIG. 2. The cover 512 is preferably liquid permeable so that bodily fluids may reach the interior of the pad for purposes of absorption. The cover 512 may be wrapped around the core 216 (as indicated by edges 514, 515). A backing sheet 516, preferably of a liquid impermeable material, may be adhered to the edges 514, 515 at the underside of the core. An adhesive containing strip, such as indicated at 520, which may have a peelable or removable cover, may be mounted to the backing sheet 516 for use in adhering the pad, for example to a user's undergarment, during use.

Figure 10:
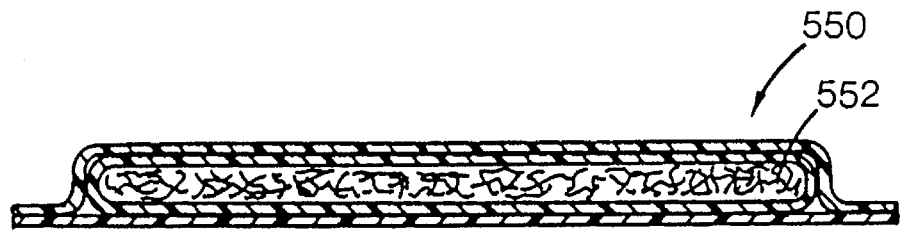
FIG. 10 is a vertical sectional view of the diaper of FIG. 9.

FIGS. 9 and 10 illustrate a conventional disposable diaper 550 with a core 552 which is comprised of fibers of the present invention with adhered superabsorbent particulate materials. These particulate materials may be confined to a target zone (for example, the front portion of a diaper indicated at 556) or of a heavier concentration in the target zone. This can be accomplished by airlaying fibers of the present invention in such a zone. Also, the core may be reactivated by melting the binder or moistening the target zone with water. The superabsorbent particles may be sprinkled on or otherwise applied to this wetted zone. As the zone dries, the particles are adhered in place.

Densification

The products such as described above, as well as webs of the fibers of the present invention, can also be densified by external application of pressure to the web. The web of Example II, for instance, could be densified by passing it through a set of calendar rolls set at 60 and 90 pli (pounds per linear inch, as in a calendar press) respectively to yield sheets with increased densities. Densification may alternatively be provided by compaction rolls or presses. The present inventors have found that densification is facilitated in the products treated with the polymeric organic binders of the present invention. Products that are treated with the binders of the present invention require less heat and pressure than untreated fibers to densify to a given density. Densification is preferably performed to produce a product that has a density of about 0.1 to 0.7 g/cc, more preferably 0.1 to 0.3 g/cc.

An example of densification using some of the binders of the present invention is given below:

EXAMPLE XXVII

Any of the products of the present invention can be formed into 550 gram/square meter sheets, six inches in diameter, in a laboratory padformer. Those pads are then passed through a set of calendar rolls set at 60 and 90 pli, respectively to yield sheets with densities of 0.3 and 0.5 g/cc.

EXAMPLE XXVIII

CCF pulp (Weyerhauser Company), containing 40% SAP by weight, was coated with 12.5% glycerin, air laid, and densified to 0.3 g/cc. Densification to this product density required 60 psi for the glycerin coated fibers. In comparison, NB-316 fibers that were not coated with glycerin required densification at 200 psi to reach a 0.3 g/cc density. Absorbent capacity was higher for the coated fibers. This comparison indicates that the fibers with glycerin bound SAP were more easily densified than the fibers that were not coated with the binder.

EXAMPLE XXIX

A 50 gram amount of polypropylene glycol is diluted with 50 grams deionized water. The resulting solution is sprayed on 321 grams of an intrafiber crosslinked cellulose fluff (HBA from Weyerhaeuser Company of Tacoma, Wash.) that was air entrained in a blender like mixing device. While the HBA fiber is still damp, 438 grams of IM 1000F (supplied by Hoechst-Celanese, of Portsmouth, Va.) is added to the mixture. The resultant mixture is then vacuumed from the blender and spread on a counter to dry overnight. Then 550 gram/square meter handsheets, six inches in diameter, are made in a laboratory padformer. Those pads are then pressed at 2000 and 3000 psi (or 60 and 90 pli in a calendar roll), respectively, to yield sheets with densities of 0.3 and 0.5 g/cc. Alternatively, pads of untreated HBA blended with 45% IM 1000F would require heating to 100° C. and pressures between 8,000 and 11,000 psi to produce pads of similar densities.

Particulate Binding

Figure 11:
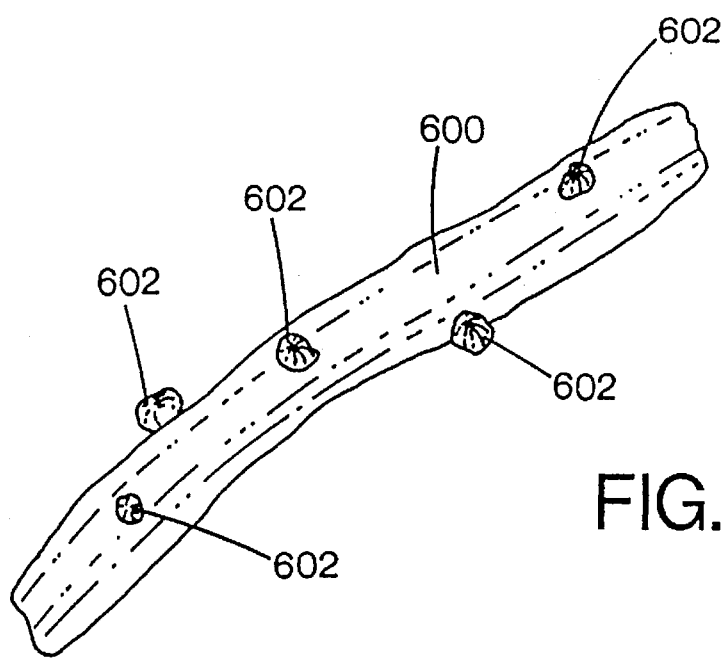
FIG. 11 is a view of an enlarged fiber with particles bonded to the fiber with the binders of the present invention.

FIG. 11 shows an isolated, enlarged cellulose fiber 600 with SAP particles 602 bound to it by a binder of the present invention. This drawing illustrates an example of the SAP retaining its discrete particulate form following binding to the fibers. Some particle to particle fusion may occur in accordance with this invention, but maintenance of a discrete particulate form excludes formation of a completely confluent film in which the particles lose their particulate identity. Such a confluent film produces gel blocking that interferes with efficient liquid absorption into the fibers.

The shown fiber 600 is elongated, and has an aspect ratio (ratio of length to width) of about 10:1.

Figure 12:
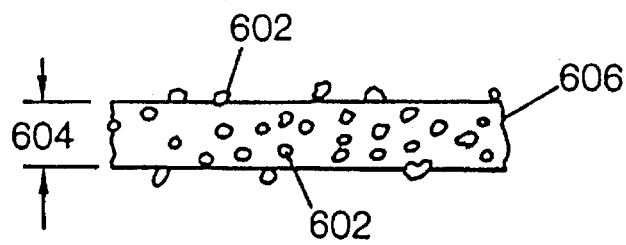
FIG. 12 is a schematic view of a cellulose mat with particles bound to all its surfaces and throughout its depth.

FIG. 12 shows the particles 602 distributed substantially uniformly throughout the depth 604 of a pad 606. The particles are also shown adhering to all the surfaces of the pad. Particles may be distributed in any desired pattern throughout the pad in accordance with this invention, and need not necessarily adhere to all surfaces or be distributed throughout the volume of the mat, or distributed uniformly.

Electron Photomicrographs

Figure 13:
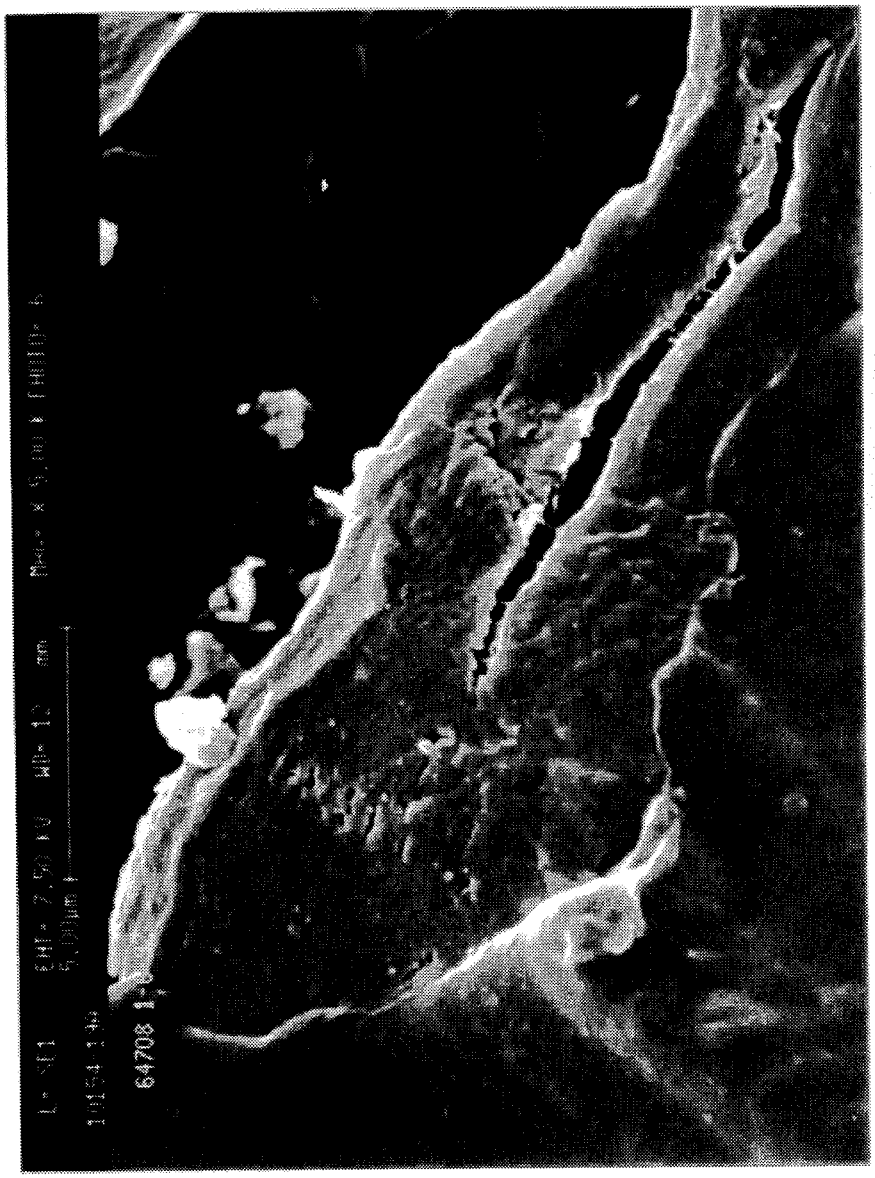
FIG. 13 is a photomicrograph of particles adhered to fibers with an ascorbic acid binder.

An electron photomicrograph of superabsorbent particles (SAP) bound to cellulose fibers with an ascorbic acid binder is shown in FIG. 13. The SAP is at the left margin of the photograph, and is fused to the fiber which occupies the central portion of the photomicrograph. The particle is seen to be fused to the fiber, and the fiber has undergone some shear damage that resulted in a fracture of the fiber. It is significant that the fiber has experienced shear damage while the particle has remained fused to the fiber, because this indicates that the particle-fiber bond formed by the ascorbic acid is very strong and resilient, resisting mechanical disruption.

Figure 14A:
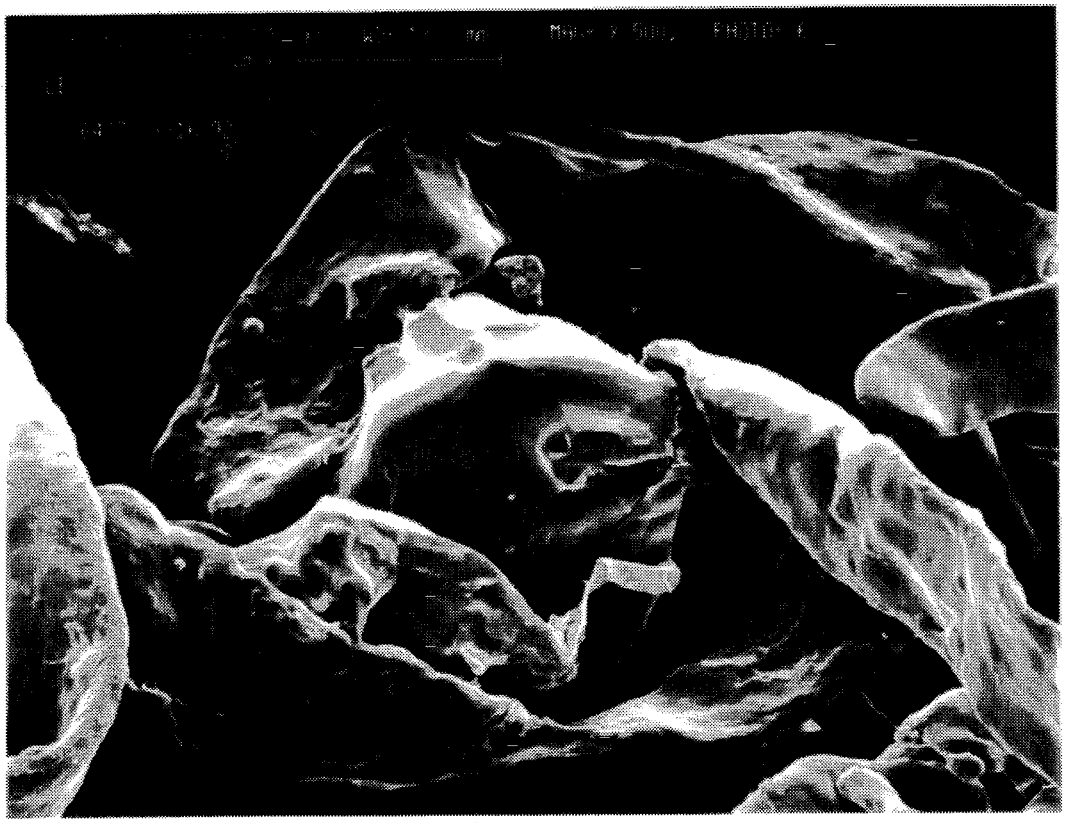
FIGS. 14A, 14B, 14C and 14D are photomicrographs of particles bound to fibers with lactose.
Figure 14B:
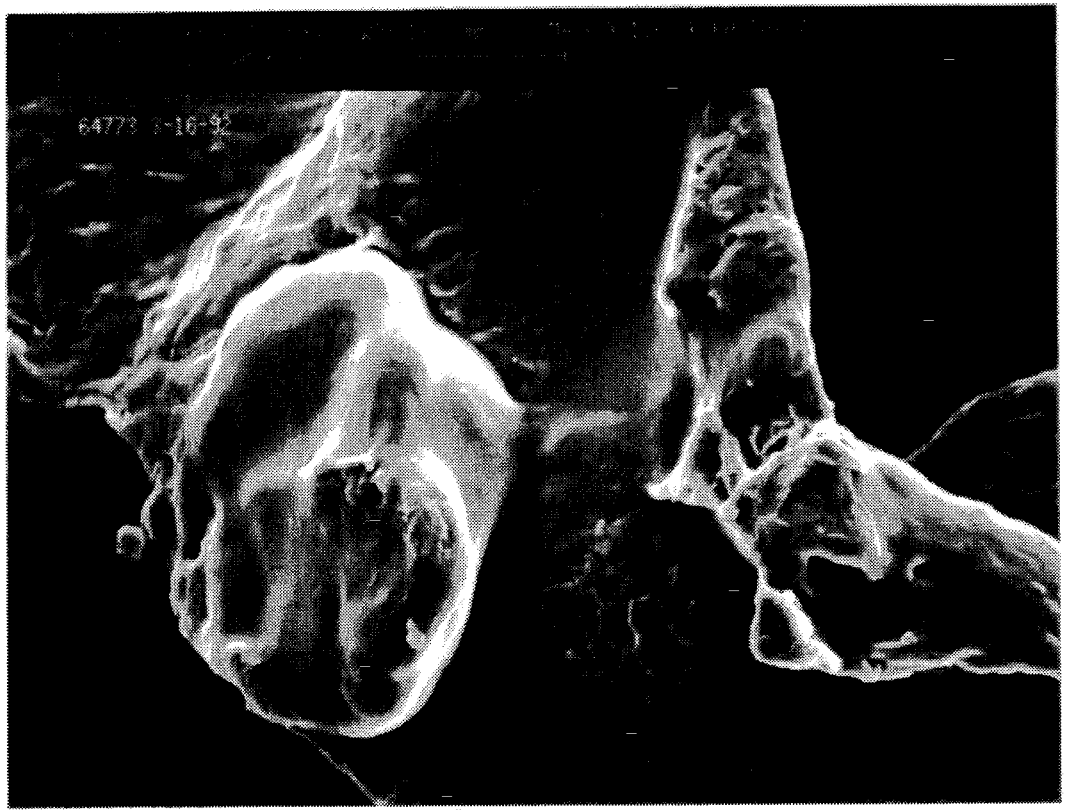
Figure 14C:
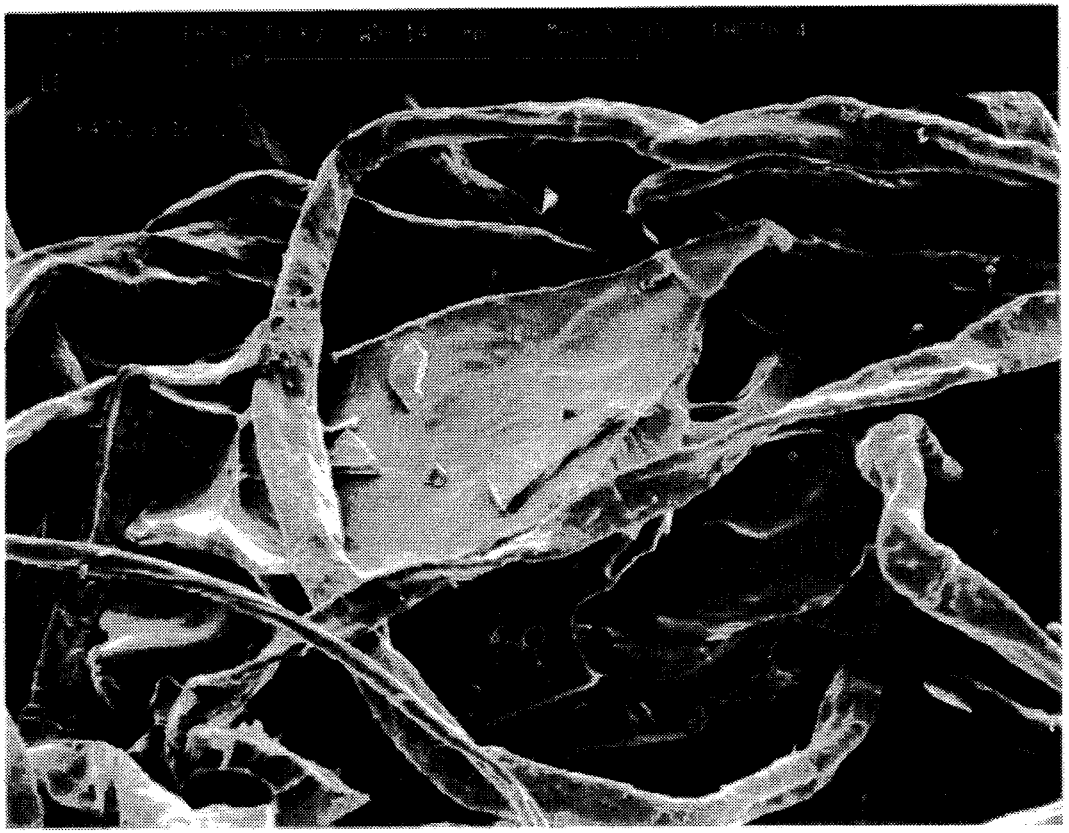
Figure 14D:

FIG. 14A–D shows several electron photomicrographs that illustrate individual particles bound to fibers with a lactose binder. FIG. 14C, for example, shows that SAP retains its individual particulate form when adhered to the fiber with a lactose binder. The particles do not form a fused confluent mass without particulate identity.

Fiber Mixtures

The fibers of the present invention, such as fiber 600, can be mixed with other types of fibers, such as that disclosed in U.S. Pat. No. 5,057,166 which is incorporated herein by reference in its entirety. The latex coated fibers of that patent can be mixed with the fibers of the present invention to produce an absorbent product that has characteristics of both types of fibers.

Additional Binder Characteristics

U.S. Pat. No. 3,903,889 discloses a process for adhering absorbent particles to pulp fibers using syrup, honey, and other polysaccharides such as dextrins. An essential requirement of these adhesive agents is that they must possess the property of being permanently pliable, and not rigidifying into a brittle film. The binders of the present invention, in contrast, are capable of functioning as a binder after solidifying into a rigid crystalline material. Even the binders of the present invention that do not rigidify into a solid (such as glycerin, low molecular weight PEG (below about 4000 g/mole) and PPG) are very hygroscopic, and can be present on fibers having a total water content of no more than 15%, or even 12%. This is in contrast to the adhesives such as honey and corn syrup disclosed in U.S. Pat. No. 3,903,889 that are not hygroscopic. Polysaccharides (such as corn syrup, honey and dextrins) are excluded as binders from some embodiments of the invention because they are a fertile substrate for microbial growth. The polysaccharide polymers are also excluded from non-polymeric embodiments of the binder. The non-polymeric saccharides, particularly monosaccharide and disaccharide embodiments of the binder, lack the high viscosity of polysaccharides that gives them their tacky texture.

Having illustrated and described the principles of the invention in many preferred embodiments, it should be apparent to those skilled in the art that the invention can be modified in arrangement and detail without departing from such principles. We claim all modifications coming within the spirit and scope of the following claims.

We claim:

1. Fibers that will adhere particles, comprising:
   fibers that have hydrogen bonding functional sites; and
   a binder mixed with the fibers, the binder having a volatility less than water, the binder also having a functional group that is capable of forming a hydrogen bond with the fibers, and a functional group that is capable of forming a hydrogen bond or coordinate covalent bond with particles, wherein the particles have a hydrogen bonding or a coordinate covalent bonding functionality, the binder having formed a non-covalent bond with the fibers and being present in an inactive form in a sufficient amount to bind the particles by non-covalent bonds to the fibers in an amount of at least 1% by weight of the binder, particles and fibers after the binder is activated.

2. The fibers of claim 1, wherein the binder is selected from the group consisting of:
   (a) a polymeric binder with repeating units and with each repeating unit having a functional group capable of forming a hydrogen bond or a coordinate covalent bond with the particles, or a hydrogen bond with the fibers; and
   (b) a non-polymeric organic binder with a functional group capable of forming a hydrogen bond or a coordinate covalent bond with the particles, and a functional group capable of forming a hydrogen bond with the fibers.

3. The fibers of claim 1, wherein the particles comprise superabsorbent particles.

4. The fibers of claim 1, wherein the fibers comprise wood pulp fibers.

5. The fibers of claim 1, wherein the particles comprise superabsorbent particles and the fibers comprise wood pulp fibers.

6. The fibers of claim 1, wherein the binder is a polymeric binder selected from the group consisting of polyethylene glycol, polypropylene glycol, poly (caprolactone) diol, polyacrylic acid, polyaldehydes, polyamides, polyamines, and copolymers thereof.

7. The fibers of claim 1, wherein the binder is selected from the group consisting of polyacrylic acid, polyamides, polyamines, and copolymers thereof.

8. The fibers of claim 1, wherein the binder is selected from the group consisting of a polyamide, a polyamine, and copolymers thereof.

9. The fibers of claim 1, wherein the binder is a non-polymeric organic binder that includes a functional group selected from the group consisting of a carboxylic acid, an aldehyde, an alcohol, an amino acid, an amide, and an amine, and wherein there are at least two functional groups on the non-polymeric organic binder selected from this group.

10. The fibers of claim 9, wherein the binder includes a carboxylic acid functional group.

11. The fibers according to claim 9, wherein the binder is selected from the group consisting of an amino acid, an amide, and an amine.

12. The fibers according to claim 9, wherein the binder is selected from the group consisting of a polycarboxylic acid, a hydroxy acid, an amino acid, and a carboxyamide.

13. The fibers of claim 9, wherein the binder is an alcohol selected from the group consisting of a polyol and an amino alcohol.

14. The fibers of claim 9, wherein the binder includes more than one amine functional group.

15. The fibers of claim 9, wherein the binder is selected from the group consisting of a hydroxyamide and a binder that includes more than one amide functional group.

16. The fibers of claim 9, wherein the binder is selected from the group consisting of glycerin, ascorbic acid, urea, glycine, pentaerythritol, a monosaccharide, a disaccharide, citric acid, tartaric acid, dipropylene glycol, and DMDHEU.

17. The fibers of claim 1, wherein the particles are selected from the group consisting of superabsorbent particles, zeolites, and antimicrobials.

18. An absorbent article comprising the fibers of claim 1.

19. The fibers of claim 1, wherein the binder can be activated by heating the fibers after applying the binder to the fibers.

20. The fibers of claim 1, wherein the binder can be activated by applying kinetic energy to the fibers after applying the binder to the fibers.

21. The fibers of claim 1, wherein the binder can be activated by adding an activating liquid to the fibers and binder.

22. The fibers of claim 1, wherein the binder is a liquid that can be activated by mechanically agitating the fibers and binder.

23. The fibers of claim 1, wherein the binder is a solid that can be activated by applying a liquid to the fibers after applying the binder to the fibers.

24. The fibers of claim 1, wherein the binder can be activated in a pattern that corresponds to a desired distribution of particles among the fibers.

25. The fibers of claim 1, wherein the fibers include intrafiber covalent bonds.

26. Fibers that will adhere particles, comprising:

fibers that have hydrogen bonding functional sites; and a non-polymeric organic binder mixed with the fibers, the non-polymeric organic binder having a volatility less than water and also having a functional group that is capable of forming a hydrogen bond with the fibers, and a functional group capable of forming a hydrogen bond or a coordinate covalent bond with particles, wherein the particles have a hydrogen bonding or a coordinate covalent bonding functionality, the non-polymeric organic binder having formed a non-covalent bond with the fibers and being present in an inactive form in a sufficient amount to bind the particles by said bonds to the fibers in an amount of at least 1% by weight of the non-polymeric organic binder, particles and fibers after the non-polymeric organic binder is activated.

27. The fibers of claim 26, wherein the binder is a non-polymeric organic binder that includes a functional group selected from the group consisting of a carboxylic acid, an aldehyde, an alcohol, an amino acid, an amide, and an amine, and wherein there are at least two functional groups on the non-polymeric organic binder selected from this group.

28. The fibers of claim 26, wherein the binder includes a carboxylic acid functional group.

29. The fibers according to claim 26, wherein the binder is selected from the group consisting of an amino acid, an amide, and an amine.

30. The fibers according to claim 26, wherein the binder is selected from the group consisting of a polycarboxylic acid, a hydroxy acid, an amino acid, and a carboxyamide.

31. The fibers of claim 26, wherein the binder is an alcohol selected from the group consisting of a polyol and an amino alcohol.

32. The fibers of claim 26, wherein the binder includes more than one amine functional group.

33. The fibers of claim 26, wherein the binder is selected from the group consisting of a hydroxyamide and a non-polymeric organic binder that includes more than one amide functional group.

34. The fibers of claim 26, wherein the non-polymeric organic binder is selected from the group consisting of glycerin, ascorbic acid, urea, glycine, pentaerythritol, a monosaccharide, a disaccharide, citric acid, tartaric acid, dipropylene glycol, and DMDHEU.

\* \* \* \* \*

UNITED STATES PATENT AND TRADEMARK OFFICE
CERTIFICATE OF CORRECTION

PATENT NO. : 5,571,618   Page 1 of 5
DATED : November 5, 1996
INVENTOR(S) : M.R. Hansen et al.

It is certified that error appears in the above-indentified patent and that said Letters Patent is hereby corrected as shown below:

| COLUMN | LINE | |
|---|---|---|
| 3 | 19–20 | "by the fibers" should read --by heating the fibers-- |
| 3 | 22 | "binder be applied" should read --binder to be applied-- |
| 3 | 28 | "binders such as" should read --binders (such as-- |
| 3 | 30 | "Invention" should read --invention-- |
| 3 | 53–54 | "the non-polymeric has" should read --the non-polymeric binder has-- |
| 4 | 22 | "hydrogen or" should read --hydrogen bonds or-- |
| 6 | 40 | "prepared" should read --pretreated-- |

UNITED STATES PATENT AND TRADEMARK OFFICE
CERTIFICATE OF CORRECTION

PATENT NO. : 5,571,618
DATED : November 5, 1996
INVENTOR(S) : M.R. Hansen et al.

It is certified that error appears in the above-indentified patent and that said Letters Patent is hereby corrected as shown below:

| | | | |
|---|---|---|---|
| 8 | 33–53 | The formula | 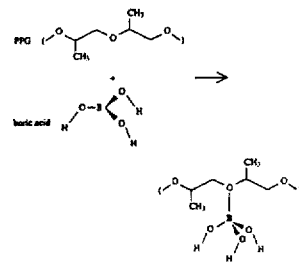 |
| | | should read | 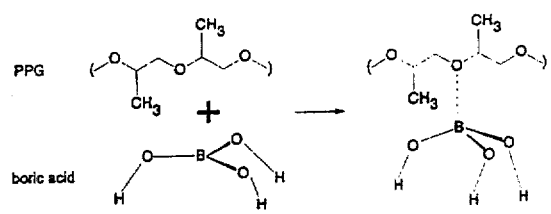 |
| 9 | 13–32 | The formula | 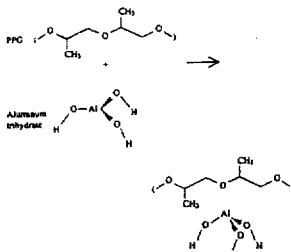 |
| | | should read | 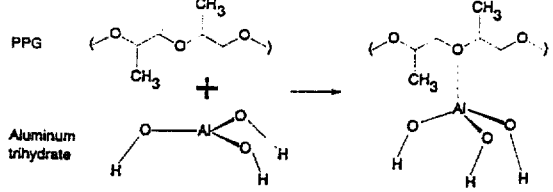 |

UNITED STATES PATENT AND TRADEMARK OFFICE
CERTIFICATE OF CORRECTION

PATENT NO. : 5,571,618  
DATED : November 5, 1996  
INVENTOR(S) : M.R. Hansen et al.

Page 3 of 5

It is certified that error appears in the above-indentified patent and that said Letters Patent is hereby corrected as shown below:

| | | |
|---|---|---|
| 11 | 63 | "Chartrausin" should read --Chartreusin-- |
| 12 | 17 | "Chloroxylanol" should read --Chloroxylenol-- |
| 13 | 6 | "a copolymer;" should read --a PPG/PEG copolymer;-- |
| 15 | 58 | "tetramet," should read --tetramer,-- |
| 16 | 48 | "other alcohols" should read --Other alcohols-- |
| 17 | 14 | "alanins," should read --alanine,-- |
| 17 | 14 | "setins," should read --serine,-- |
| 17 | 23 | "hydrogen bends" should read --hydrogen bonds-- |

UNITED STATES PATENT AND TRADEMARK OFFICE
CERTIFICATE OF CORRECTION

PATENT NO. : 5,571,618
DATED : November 5, 1996
INVENTOR(S) : M.R. Hansen et al.

Page 4 of 5

It is certified that error appears in the above-indentified patent and that said Letters Patent is hereby corrected as shown below:

19-20    Top of page    The formula

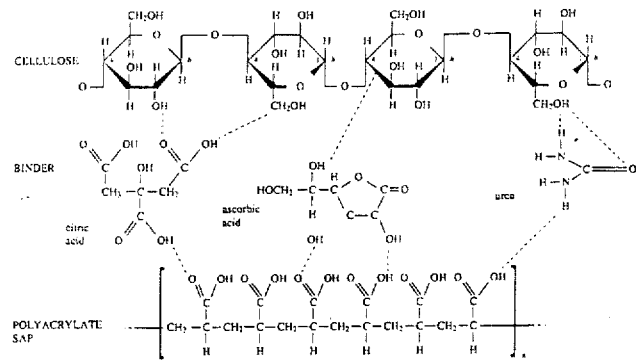

should read

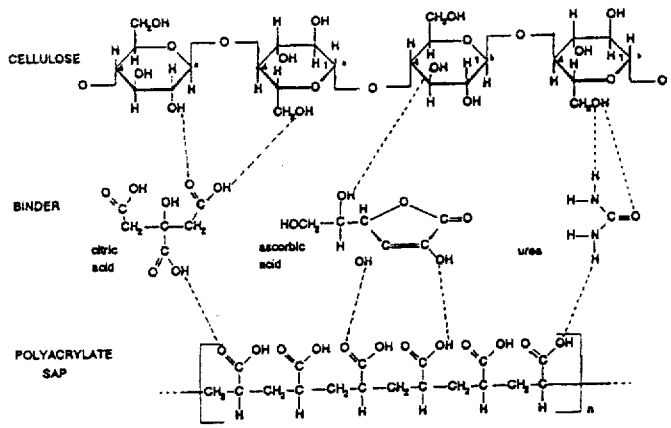

UNITED STATES PATENT AND TRADEMARK OFFICE
CERTIFICATE OF CORRECTION

PATENT NO. : 5,571,618

DATED : November 5, 1996

INVENTOR(S) : M.R. Hansen et al.

It is certified that error appears in the above-indentified patent and that said Letters Patent is hereby corrected as shown below:

| 19 | 37 | "amimo alcohol," should read --amino alcohol,-- |
| 23 | 67 | After "fibers" delete --.-- |
| 31 | 35 | "pKa," should read --pK$_a$-- |
| 36 | 55 | "certain" should read --Certain-- |

Signed and Sealed this

Fifth Day of August, 1997

Attest:

Attesting Officer

BRUCE LEHMAN

Commissioner of Patents and Trademarks